United States Patent
Sacks et al.

(10) Patent No.: US 12,295,886 B2
(45) Date of Patent: May 13, 2025

(54) PROTECTION FOR DIRECT SELECTIVE LASER TRABECULOPLASTY

(71) Applicant: BELKIN LASER LTD., Yavne (IL)

(72) Inventors: Zachary Sacks, Modiin (IL); Daria Lemann-Blumenthal, Bitzaron (IL)

(73) Assignee: Belkin Vision Ltd., Yavne (IL)

( * ) Notice: Subject to any disclaimer, the term of this patent is extended or adjusted under 35 U.S.C. 154(b) by 942 days.

(21) Appl. No.: 17/273,323

(22) PCT Filed: Oct. 23, 2019

(86) PCT No.: PCT/IB2019/059058
§ 371 (c)(1),
(2) Date: Mar. 4, 2021

(87) PCT Pub. No.: WO2020/089737
PCT Pub. Date: May 7, 2020

(65) Prior Publication Data
US 2021/0322214 A1    Oct. 21, 2021

Related U.S. Application Data

(60) Provisional application No. 62/751,629, filed on Oct. 28, 2018.

(51) Int. Cl.
*A61F 9/008* (2006.01)
*A61F 9/009* (2006.01)

(52) U.S. Cl.
CPC ............ *A61F 9/0084* (2013.01); *A61F 9/009* (2013.01); *A61F 2009/00846* (2013.01); *A61F 2009/00868* (2013.01); *A61F 2009/00891* (2013.01)

(58) Field of Classification Search
CPC .................... A61F 9/0084; A61F 9/009; A61F 2009/00846; A61F 2009/00868; A61F 2009/00891
See application file for complete search history.

(56) References Cited

U.S. PATENT DOCUMENTS 2,635,502 A    4/1953    Richards
3,594,072 A    7/1971    Feather
(Continued)

FOREIGN PATENT DOCUMENTS

AU    2015210430 A1    9/2015
AU    2015315113 B2    3/2016
(Continued)

OTHER PUBLICATIONS

SG Application # 11202010437T Office Action dated May 13, 2022.
(Continued)

*Primary Examiner* — Shirley X Jian
(74) *Attorney, Agent, or Firm* — Meitar Patents Ltd.; Daniel Kligler

(57) ABSTRACT

An apparatus includes an optical unit (30), including a light source (66), one or more beam-directing elements (50, 56), and a radiation source (48). The radiation source is configured to irradiate an eye (25) of a patient (22) with one or more treatment beams (52) by emitting the treatment beams toward the beam-directing elements, while the eye fixates on the light source by virtue of the light source transmitting visible light (68). The apparatus further includes an optical filter (70) configured to inhibit passage of the treatment beams, but not the visible light, therethrough, while interposing between the beam-directing elements and a pupil (104) of the eye. Other embodiments are also described.

40 Claims, 5 Drawing Sheets

(56) References Cited

U.S. PATENT DOCUMENTS

| | | | |
|---|---|---|---|
| 4,587,257 A | 5/1986 | DeSantis | |
| 4,641,349 A | 2/1987 | Flom et al. | |
| 4,718,418 A | 1/1988 | L'Esperance | |
| 4,848,894 A | 7/1989 | Buser et al. | |
| 4,941,093 A | 7/1990 | Marshall et al. | |
| 4,966,452 A | 10/1990 | Shields et al. | |
| 5,049,147 A | 9/1991 | Danon | |
| 5,123,902 A | 6/1992 | Muller et al. | |
| 5,141,506 A * | 8/1992 | York | A61F 9/00804 606/5 |
| 5,151,909 A | 9/1992 | Davenport et al. | |
| 5,152,760 A | 10/1992 | Latina | |
| 5,370,641 A | 12/1994 | O'Donnell, Jr. | |
| 5,422,899 A | 6/1995 | Freiberg et al. | |
| 5,479,222 A | 12/1995 | Volk et al. | |
| 5,537,164 A | 7/1996 | Smith | |
| 5,549,596 A | 8/1996 | Latina | |
| 5,598,007 A | 1/1997 | Bunce et al. | |
| 5,786,883 A | 7/1998 | Miller et al. | |
| 5,865,830 A | 2/1999 | Parel et al. | |
| 5,982,789 A | 11/1999 | Marshall et al. | |
| 6,027,216 A | 2/2000 | Guyton et al. | |
| 6,030,376 A * | 2/2000 | Arashima | A61B 3/113 606/4 |
| 6,033,396 A | 3/2000 | Huang et al. | |
| 6,059,772 A | 5/2000 | Hsia et al. | |
| 6,096,029 A | 8/2000 | O'Donnell, Jr. | |
| 6,099,521 A | 8/2000 | Shadduck | |
| 6,099,522 A | 8/2000 | Knopp et al. | |
| 6,146,375 A | 11/2000 | Juhasz et al. | |
| 6,159,202 A * | 12/2000 | Sumiya | A61F 9/008 606/4 |
| 6,210,399 B1 | 4/2001 | Parel et al. | |
| 6,258,082 B1 | 7/2001 | Lin | |
| 6,263,879 B1 | 7/2001 | Lin | |
| 6,267,752 B1 | 7/2001 | Svetliza | |
| 6,267,756 B1 | 7/2001 | Feuerstein et al. | |
| 6,286,960 B1 * | 9/2001 | Tomita | A61B 3/0075 351/245 |
| 6,319,274 B1 | 11/2001 | Shadduck | |
| 6,325,792 B1 | 12/2001 | Swinger et al. | |
| 6,414,980 B1 | 7/2002 | Wang et al. | |
| 6,454,763 B1 | 9/2002 | Motter et al. | |
| 6,514,241 B1 | 2/2003 | Hsia et al. | |
| 6,530,916 B1 | 3/2003 | Shimmick | |
| 6,569,104 B2 | 5/2003 | Ono et al. | |
| 6,585,723 B1 * | 7/2003 | Sumiya | A61F 9/00804 606/5 |
| 6,673,062 B2 | 1/2004 | Yee et al. | |
| 6,676,655 B2 | 1/2004 | McDaniel | |
| 6,685,317 B2 | 2/2004 | Su et al. | |
| 6,698,886 B2 | 3/2004 | Pollack et al. | |
| 6,736,806 B2 | 5/2004 | Ruiz et al. | |
| 6,761,713 B2 | 7/2004 | Teichmann | |
| 6,899,707 B2 | 5/2005 | Scholler et al. | |
| 6,942,656 B2 | 9/2005 | Pawlowski et al. | |
| 6,948,815 B2 | 9/2005 | Neuberger | |
| 6,979,328 B2 | 12/2005 | Baerveldt et al. | |
| 7,027,233 B2 | 4/2006 | Goldstein et al. | |
| 7,252,661 B2 | 8/2007 | Nguyen et al. | |
| 7,282,046 B2 | 10/2007 | Simon | |
| 7,353,829 B1 | 4/2008 | Wachter et al. | |
| 7,371,230 B2 | 5/2008 | Webb et al. | |
| 7,693,259 B2 | 4/2010 | Gertner | |
| 7,792,249 B2 | 9/2010 | Gertner et al. | |
| 8,004,764 B2 | 8/2011 | Artsyukhovich et al. | |
| 8,048,065 B2 | 11/2011 | Grecu et al. | |
| 8,109,635 B2 | 2/2012 | Allon et al. | |
| 8,160,113 B2 | 4/2012 | Adams et al. | |
| 8,403,921 B2 | 3/2013 | Palanker et al. | |
| 8,442,185 B2 | 5/2013 | Gertner et al. | |
| 8,465,478 B2 | 6/2013 | Frey et al. | |
| 8,475,433 B2 | 7/2013 | Mrochen et al. | |
| 8,545,020 B2 | 10/2013 | Liesfeld et al. | |
| 8,568,393 B2 | 10/2013 | Palanker | |
| 8,630,388 B2 | 1/2014 | Gertner et al. | |
| 8,679,100 B2 | 3/2014 | Raksi et al. | |
| 8,708,491 B2 | 4/2014 | Frey et al. | |
| 8,709,029 B2 | 4/2014 | Griffis, III et al. | |
| 8,771,261 B2 | 7/2014 | Andersen et al. | |
| 8,811,657 B2 | 8/2014 | Teiwes et al. | |
| 8,845,625 B2 | 9/2014 | Angeley et al. | |
| 8,903,468 B2 | 12/2014 | Peyman | |
| 8,920,407 B2 | 12/2014 | Raksi et al. | |
| 8,939,965 B2 | 1/2015 | Liesfeld et al. | |
| 8,968,279 B2 | 3/2015 | Arnoldussen | |
| 8,995,618 B2 | 3/2015 | Gertner | |
| 9,055,896 B2 | 6/2015 | Amthor et al. | |
| 9,192,780 B2 | 11/2015 | McDaniel | |
| 9,220,407 B2 | 12/2015 | Yam et al. | |
| 9,351,878 B2 | 5/2016 | Muehlhoff et al. | |
| 9,480,599 B2 | 11/2016 | Degani et al. | |
| 9,495,743 B2 | 11/2016 | Angeley et al. | |
| 9,504,609 B2 | 11/2016 | Kurtz | |
| 9,532,712 B2 | 1/2017 | Liesfeld et al. | |
| 9,622,911 B2 | 4/2017 | Rubinfeld et al. | |
| 9,782,232 B1 | 10/2017 | Papac | |
| 9,849,032 B2 | 12/2017 | Schuele et al. | |
| 9,849,034 B2 | 12/2017 | Artsyukhovich et al. | |
| 9,877,633 B2 | 1/2018 | Zhao et al. | |
| 9,889,043 B2 | 2/2018 | Frey et al. | |
| 9,968,483 B2 | 5/2018 | Takeda et al. | |
| 10,022,457 B2 | 7/2018 | Peyman | |
| 10,064,757 B2 | 9/2018 | Berlin | |
| 10,143,590 B2 | 12/2018 | Dick et al. | |
| 10,244,991 B2 | 4/2019 | Shademan et al. | |
| 10,258,507 B2 | 4/2019 | Gonzalez et al. | |
| 10,278,865 B2 | 5/2019 | Luttrull et al. | |
| 10,299,961 B2 | 5/2019 | Luttrull et al. | |
| 10,363,169 B2 | 7/2019 | Belkin et al. | |
| 10,441,465 B2 | 10/2019 | Hart et al. | |
| 10,449,091 B2 | 10/2019 | Angeley et al. | |
| 10,456,209 B2 | 10/2019 | Peyman | |
| 10,478,342 B2 | 11/2019 | Dick et al. | |
| 10,524,656 B2 | 1/2020 | Wiltberger et al. | |
| 10,617,564 B1 | 4/2020 | Andersen et al. | |
| 10,684,449 B2 | 6/2020 | Curatu et al. | |
| 10,702,416 B2 | 7/2020 | Belkin et al. | |
| 10,849,789 B2 | 12/2020 | Dewey et al. | |
| 10,925,768 B2 | 2/2021 | Charles | |
| 11,564,836 B2 * | 1/2023 | Belkin | A61F 9/0079 |
| 11,890,051 B2 * | 2/2024 | Heacock | A61B 3/1208 |
| 12,109,149 B2 * | 10/2024 | Sacks | A61F 9/00823 |
| 2001/0027314 A1 | 10/2001 | Peyman | |
| 2002/0013572 A1 * | 1/2002 | Berlin | A61F 2/14 606/4 |
| 2002/0013573 A1 | 1/2002 | Telfair et al. | |
| 2002/0026179 A1 * | 2/2002 | Toh | A61F 9/00804 606/5 |
| 2003/0179344 A1 | 9/2003 | Van de Velde | |
| 2003/0225398 A1 | 12/2003 | Zepkin et al. | |
| 2004/0039378 A1 | 2/2004 | Lin | |
| 2004/0059321 A1 | 3/2004 | Knopp et al. | |
| 2004/0196431 A1 | 10/2004 | Farberov | |
| 2005/0096639 A1 | 5/2005 | Slatkine et al. | |
| 2005/0107774 A1 | 5/2005 | Lin | |
| 2005/0185138 A1 | 8/2005 | Wong et al. | |
| 2005/0197655 A1 * | 9/2005 | Telfair | A61B 18/20 606/5 |
| 2005/0254009 A1 | 11/2005 | Baker et al. | |
| 2005/0286019 A1 | 12/2005 | Wiltberger et al. | |
| 2005/0288745 A1 | 12/2005 | Andersen et al. | |
| 2006/0100677 A1 | 5/2006 | Blumenkranz et al. | |
| 2006/0176913 A1 | 8/2006 | Souhaite et al. | |
| 2006/0195076 A1 | 8/2006 | Blumenkranz et al. | |
| 2006/0224147 A1 * | 10/2006 | Abe | A61F 9/008 606/4 |
| 2006/0265030 A1 | 11/2006 | McDaniel | |
| 2007/0081166 A1 | 4/2007 | Brown et al. | |
| 2007/0129709 A1 | 6/2007 | Andersen et al. | |
| 2007/0159600 A1 | 7/2007 | Gil et al. | |
| 2007/0213693 A1 | 9/2007 | Plunkett | |

(56) References Cited

U.S. PATENT DOCUMENTS

| | | |
|---|---|---|
| 2008/0027418 A1* | 1/2008 | Berry .................. A61F 9/008 606/5 |
| 2008/0089481 A1 | 4/2008 | Gertner |
| 2008/0108934 A1 | 5/2008 | Berlin et al. |
| 2008/0161781 A1 | 7/2008 | McArdle et al. |
| 2008/0167642 A1 | 7/2008 | Palanker et al. |
| 2008/0204658 A1 | 8/2008 | Van Saarloos |
| 2008/0234667 A1 | 9/2008 | Lang et al. |
| 2008/0255546 A1 | 10/2008 | Orbachevski |
| 2009/0137993 A1 | 5/2009 | Kurtz |
| 2009/0157062 A1 | 6/2009 | Hauger et al. |
| 2009/0247997 A1 | 10/2009 | Watanabe et al. |
| 2010/0002837 A1 | 1/2010 | Gertner et al. |
| 2010/0057059 A1 | 3/2010 | Makino |
| 2010/0076419 A1 | 3/2010 | Chew et al. |
| 2010/0142767 A1 | 6/2010 | Fleming |
| 2010/0324543 A1 | 12/2010 | Kurtz et al. |
| 2011/0144627 A1 | 6/2011 | Smith et al. |
| 2011/0172649 A1 | 7/2011 | Schuele et al. |
| 2011/0190741 A1 | 8/2011 | Deisinger et al. |
| 2012/0016349 A1 | 1/2012 | Brownell |
| 2012/0050308 A1 | 3/2012 | Nakano et al. |
| 2012/0083772 A1 | 4/2012 | Rubinfeld et al. |
| 2012/0089134 A1 | 4/2012 | Horvath et al. |
| 2012/0259321 A1 | 10/2012 | Vera et al. |
| 2012/0283557 A1 | 11/2012 | Berlin |
| 2013/0103011 A1 | 4/2013 | Grant et al. |
| 2013/0123761 A1 | 5/2013 | Belkin et al. |
| 2013/0204236 A1 | 8/2013 | Awdeh |
| 2013/0218145 A1 | 8/2013 | Belkin et al. |
| 2013/0289450 A1 | 10/2013 | Homer |
| 2013/0317570 A1 | 11/2013 | Luttrull et al. |
| 2014/0094785 A1 | 4/2014 | Charles |
| 2014/0114297 A1 | 4/2014 | Woodley et al. |
| 2014/0128731 A1 | 5/2014 | Gonzalez et al. |
| 2014/0128851 A1 | 5/2014 | Wysopal |
| 2014/0128852 A1 | 5/2014 | Gooding et al. |
| 2014/0135747 A1 | 5/2014 | Donitzky et al. |
| 2014/0135753 A1 | 5/2014 | Feklistov et al. |
| 2014/0276681 A1 | 9/2014 | Schuele et al. |
| 2014/0307077 A1 | 10/2014 | Prabhakar |
| 2015/0164635 A1 | 6/2015 | Renke |
| 2015/0223683 A1 | 8/2015 | Davidovics et al. |
| 2015/0266706 A1 | 9/2015 | Hashimoto |
| 2015/0272782 A1 | 10/2015 | Schuele et al. |
| 2015/0313759 A1 | 11/2015 | Vera et al. |
| 2016/0008169 A1 | 1/2016 | Yu |
| 2016/0008172 A1 | 1/2016 | Kahook |
| 2016/0067035 A1 | 3/2016 | Gontijo et al. |
| 2016/0067087 A1 | 3/2016 | Tedford et al. |
| 2016/0089269 A1 | 3/2016 | Horvath et al. |
| 2016/0095752 A1 | 4/2016 | Srinivasan et al. |
| 2016/0113816 A1 | 4/2016 | Herekar et al. |
| 2016/0346126 A1 | 12/2016 | Luttrull et al. |
| 2016/0354241 A1 | 12/2016 | Mordaunt et al. |
| 2016/0367399 A1 | 12/2016 | Goldshleger et al. |
| 2017/0000647 A1 | 1/2017 | Schuele et al. |
| 2017/0038284 A1 | 2/2017 | Nemati |
| 2017/0087014 A1 | 3/2017 | Potter, Jr. et al. |
| 2017/0127938 A1 | 5/2017 | Izatt et al. |
| 2017/0184875 A1 | 6/2017 | Newman |
| 2017/0246033 A1 | 8/2017 | Bor et al. |
| 2017/0340483 A1 | 11/2017 | Rill et al. |
| 2017/0360604 A1 | 12/2017 | Bach et al. |
| 2018/0085257 A1 | 3/2018 | Horvath et al. |
| 2018/0104477 A1 | 4/2018 | Kurtz et al. |
| 2018/0125708 A1 | 5/2018 | Bohme et al. |
| 2018/0168737 A1 | 6/2018 | Ren et al. |
| 2018/0207029 A1 | 7/2018 | Herekar et al. |
| 2018/0214305 A1 | 8/2018 | Schuele et al. |
| 2018/0221199 A1 | 8/2018 | Heacock |
| 2018/0235462 A1 | 8/2018 | Gooi et al. |
| 2018/0344527 A1 | 12/2018 | Palanker et al. |
| 2019/0078073 A1 | 3/2019 | Streeter et al. |
| 2019/0099291 A1 | 4/2019 | Herekar et al. |
| 2019/0105200 A1 | 4/2019 | Hipsley |
| 2019/0105519 A1 | 4/2019 | Herekar et al. |
| 2019/0117459 A1 | 4/2019 | Berlin |
| 2019/0142636 A1 | 5/2019 | Tedford et al. |
| 2019/0151146 A1 | 5/2019 | Kim |
| 2019/0247225 A1 | 8/2019 | Stobrawa et al. |
| 2019/0269554 A1 | 9/2019 | Goldshleger et al. |
| 2019/0343680 A1 | 11/2019 | Belkin et al. |
| 2019/0344076 A1 | 11/2019 | Irazoqui et al. |
| 2019/0358085 A1 | 11/2019 | Fu et al. |
| 2020/0038245 A1 | 2/2020 | Hart et al. |
| 2020/0078216 A1 | 3/2020 | Raksi |
| 2020/0093639 A1 | 3/2020 | McCall, Jr. |
| 2020/0107724 A1 | 4/2020 | Wiltberger et al. |
| 2020/0146887 A1 | 5/2020 | Horvath et al. |
| 2020/0306080 A1 | 10/2020 | Herekar et al. |
| 2020/0345546 A1 | 11/2020 | Belkin et al. |
| 2020/0352785 A1 | 11/2020 | Holland et al. |
| 2020/0360187 A1 | 11/2020 | Schuele et al. |
| 2020/0379216 A1 | 12/2020 | Curatu et al. |
| 2021/0338484 A1 | 11/2021 | Hipsley |
| 2022/0031503 A1 | 2/2022 | Dorin et al. |
| 2023/0201037 A1 | 6/2023 | Barrett et al. |
| 2023/0226372 A1 | 7/2023 | Herekar et al. |

FOREIGN PATENT DOCUMENTS

| | | |
|---|---|---|
| AU | 2017258835 B2 | 11/2017 |
| CA | 2640203 A1 | 8/2007 |
| CN | 1579351 A | 2/2005 |
| CN | 101411607 A | 4/2009 |
| CN | 201537172 U | 8/2010 |
| CN | 102193182 A | 9/2011 |
| CN | 105138996 A | 12/2015 |
| CN | 205698218 U | 11/2016 |
| DE | 202016006265 U1 | 3/2017 |
| EP | 0224322 A1 | 6/1987 |
| EP | 0651982 A1 | 5/1995 |
| EP | 0689811 A1 | 1/1996 |
| EP | 1602321 A1 | 12/2005 |
| EP | 2301421 A1 | 3/2011 |
| EP | 2301424 B1 | 3/2011 |
| EP | 2301425 B1 | 3/2011 |
| EP | 2602005 A1 | 6/2013 |
| EP | 1856774 B1 | 6/2016 |
| EP | 2695016 B1 | 3/2017 |
| EP | 2992931 B1 | 8/2017 |
| EP | 2391318 B1 | 12/2017 |
| EP | 3329839 A1 | 6/2018 |
| EP | 2729099 B1 | 11/2019 |
| EP | 3191040 B1 | 7/2020 |
| EP | 3517081 B1 | 11/2020 |
| EP | 2854729 B1 | 3/2021 |
| FR | 2655837 A1 | 6/1991 |
| JP | 2007151739 A | 6/2007 |
| JP | 2010148635 A | 7/2010 |
| JP | 2016013255 A | 1/2016 |
| JP | 6083823 B2 | 2/2017 |
| JP | 2018051210 A | 4/2018 |
| KR | 20180106113 A | 10/2018 |
| KR | 20190022216 A | 3/2019 |
| RU | 2499582 C1 | 11/2013 |
| RU | 2553507 C1 | 6/2015 |
| WO | 9216259 A1 | 10/1992 |
| WO | 1993012727 A1 | 7/1993 |
| WO | 9316631 A1 | 9/1993 |
| WO | 9412092 A1 | 6/1994 |
| WO | 9416425 A1 | 7/1994 |
| WO | 9515134 A1 | 6/1995 |
| WO | 1998022016 A2 | 5/1998 |
| WO | 9918868 A1 | 4/1999 |
| WO | 0195842 A1 | 12/2001 |
| WO | 02064031 A2 | 8/2002 |
| WO | 02087442 A1 | 11/2002 |
| WO | 2014018104 A1 | 1/2004 |
| WO | 2004027487 A1 | 4/2004 |
| WO | 2006119349 A2 | 11/2006 |
| WO | 2006119584 A1 | 11/2006 |
| WO | 2006128038 A2 | 11/2006 |

(56) References Cited

FOREIGN PATENT DOCUMENTS

| | | | |
|---|---|---|---|
| WO | 2007103349 | A2 | 9/2007 |
| WO | 2008112236 | A1 | 9/2008 |
| WO | 2008118198 | A2 | 10/2008 |
| WO | 2010094353 | A1 | 8/2010 |
| WO | 2010113193 | A1 | 10/2010 |
| WO | 2011017002 | A2 | 2/2011 |
| WO | 2011163508 | A2 | 6/2011 |
| WO | 2011085274 | A1 | 7/2011 |
| WO | 2011151812 | A1 | 12/2011 |
| WO | 2013004255 | A1 | 1/2013 |
| WO | 2013035091 | A1 | 3/2013 |
| WO | 2013059481 | A1 | 4/2013 |
| WO | 2013059564 | A1 | 4/2013 |
| WO | 2013122711 | A1 | 8/2013 |
| WO | 2013165689 | A1 | 11/2013 |
| WO | 2014025862 | A1 | 2/2014 |
| WO | 2014132162 | A1 | 9/2014 |
| WO | 2014191031 | A1 | 12/2014 |
| WO | 2015069197 | A1 | 5/2015 |
| WO | 2015130821 | A2 | 9/2015 |
| WO | 2016018864 | A1 | 2/2016 |
| WO | 2016058931 | A2 | 4/2016 |
| WO | 2016156760 | A1 | 10/2016 |
| WO | 2016187436 | A1 | 11/2016 |
| WO | 2016207739 | A1 | 12/2016 |
| WO | 2017023296 | A1 | 2/2017 |
| WO | 2017031570 | A1 | 3/2017 |
| WO | 2017069819 | A1 | 4/2017 |
| WO | 2018005796 | A1 | 1/2018 |
| WO | 2018021780 | A1 | 2/2018 |
| WO | 2018049246 | A1 | 3/2018 |
| WO | 2018152020 | A1 | 8/2018 |
| WO | 2018232397 | A1 | 12/2018 |
| WO | 2019109125 | A1 | 6/2019 |
| WO | 2020008323 | A1 | 1/2020 |
| WO | 2020012841 | A1 | 1/2020 |
| WO | 2020018242 | A1 | 1/2020 |
| WO | 2020018436 | A1 | 1/2020 |
| WO | 2020050308 | A1 | 3/2020 |
| WO | 202093060 | A2 | 5/2020 |
| WO | 2020089737 | A1 | 5/2020 |
| WO | 2020183342 | A1 | 9/2020 |
| WO | 2021026538 | A1 | 2/2021 |
| WO | 2021048723 | A1 | 3/2021 |
| WO | 2021170664 | A1 | 9/2021 |
| WO | 2022223690 | A1 | 10/2022 |

OTHER PUBLICATIONS

U.S. Appl. No. 16/935,236 Office Action dated Jun. 16, 2022.
EP Application # 19877990.2 Search Report dated Jul. 5, 2022.
Gazzard et al., "Selective Laser Trabeculoplasty versus Drops for Newly Diagnosed Ocular Hypertension and Glaucoma: The LiGHT RCT," Health Technology Assessment, NHS, vol. 23, issue 31, pp. 1-132, Jun. 2019.
Kelley et al., "Stem Cells in the Trabecular Meshwork: Present and Future Promises," Experimental Eye Research, vol. 88, issue 4, pp. 747-751, Apr. 2009.
Dueker et al., "Stimulation of Cell Division by Argon and Nd:YAG Laser Trabeculoplasty in Cynomolgus Monkeys," Investigative Ophthalmology & Visual Science, vol. 31, No. 1, pp. 115-124, year 1990.
Nowell et al., "Corneal Epithelial Stem Cells and their Niche at a Glance," Cell Science at a Glance, vol. 130, Issue 6, pp. 1021-1025, year 2017.
Kim et al., "Diagnosis of Corneal Limbal Stem Cell Deficiency," Current Opinion in Ophthalmology, Wolters Kluwer Health, Inc., vol. 28, No. 4, pp. 355-362, Jul. 2017.
Gonzalez et al., "Limbal Stem Cells: Identity, Developmental Origin, and Therapeutic Potential," WIREs Developmental Biology, Wiley, vol. 7, issue 2, pp. 1-23, Mar. 2018.
Sepehr, "Corneal Endothelial Cell Dysfunction: Etiologies and Management," Therapeutic Advances in Opthalmology, pp. 1-19, year 2018.
Espana et al., "Existence of Corneal Endothelial Slow-Cycling Cells," Investigative Ophthalmology & Visual Science, vol. 56, No. 6, pp. 3827-3837, Jun. 2015.
Walshe et al., "Serial Explant Culture Provides Novel Insights into the Potential Location and Phenotype of Corneal Endothelial Progenitor Cells," Experimental Eye Research, vol. 127, pp. 9-13, year 2014.
Pinnamaneni et al., "Concise Review: Stem Cells in the Corneal Stroma," Stem Cells, vol. 30, issue 6, pp. 1059-1063, year 2012.
AU Application # 2019297135 Office Action dated Sep. 30, 2021.
International Application # PCT/IB2021/054187 Search Report dated Jul. 30, 2021.
U.S. Appl. No. 17/254,279 Office Action dated Dec. 20, 2021.
AU Application # 2019297135 Office Action dated Jan. 5, 2022.
U.S. Appl. No. 16/935,236 Office Action dated Jan. 6, 2022.
IN Application # 202147003401 Office Action dated Jan. 13, 2022.
CN Application # 201980043641.6 Office Action dated Feb. 18, 2022.
EP Application # 19830473.5 Search Report dated Feb. 28, 2022.
IN Application # 201948052117 Office Action dated Feb. 16, 2022.
Katta et al., "Optical Coherence Tomography Image-Guided Smart Laser Knife for Surgery," Lasers in Surgery and Medicine, Wiley Online Library, pp. 1-11, Jul. 2017.
Barnes et al., "Control of Intraocular Pressure Elevations after Argon Laser Trabeculoplasty: Comparison of Brimonidine 0.2% to Apraclonidine 1.0%," Opthalmology, vol. 106, No. 10, pp. 2033-2037, year 1999.
Yakopson et al., "Brimonidine 0.1% vs. Apraclonidine 0.5% for Prevention of Intraocular Pressure Elevation after Selective Laser Trabeculoplasty," Investigative Ophthalmology & Visual Science, vol. 49, p. 1234, May 2008.
Kim et at., "Effect of Prophylactic Topical Brimonidine (0.15%) Administration on the Development of Subconjunctival Hemorrhage after Intravitreal Injection," Retina, The Journal for Retinal and Vitreous Diseases, vol. 31, No. 2, pp. 389-392, year 2011.
Hong et al., "Effect of Prophylactic Brimonidine Instillation on Bleeding during Strabismus Surgery in Adults," American Journal of Ophthalmology, vol. 144, No. 3, pp. 469-470, Sep. 2007.
Goldsmith et al., "Anterior Chamber Width Measurement by High-Speed Optical Coherence Tomography," Ophthalmology, vol. 112, No. 2, pp. 238-244, year 2005.
Norden, "Effect of Prophilactic Brimonidine on Bleeding Complications and Flap Adherence After Laser in situ Keratomileusis," Journal of Refractive Surgery, vol. 18, No. 4, pp. 468-471, Jul./Aug. 2002.
Kohnen et al., "Internal Anterior Chamber Diameter using Optical Coherence Tomography Compared with White-To-White Distances using Automated Measurements," Journal of Cataract & Refractive Surgery, vol. 32, pp. 1809-1813, Nov. 2006.
Zhang et al., "Perioperative Medications for Preventing Temporarily Increased Intraocular Pressure after Laser Trabeculoplasty (Review)," Cochrane Database of Systematic Reviews 2017, issue 2, pp. 1-117, year 2017.
EP Application # 20201567.3 Search Report dated Jun. 22, 2021.
U.S. Appl. No. 16/420,194 Office Action dated Jul. 22, 2021.
Gophotonics, "NL200 series," Data Sheet, pp. 1-3, Jun. 29, 2017.
EP Application # 20201567.3 Office Action dated Jun. 6, 2023.
JP Application # 2020561860 Office Action dated Jun. 13, 2023.
JP Application # 2021516473 Office Action dated Jun. 20, 2023.
CN Application # 2020800563096 Office Action dated Jul. 1, 2023.
EP Application # 20864109.2 Search Report dated Aug. 10, 2023.
CN Application # 2019800436416 Office Action dated Aug. 17, 2022.
U.S. Appl. No. 16/935,236 Office Action dated Sep. 15, 2022.
U.S. Appl. No. 16/420,194 Office Action dated Aug. 5, 2022.
Root, "How to perform a Laser Iridotomy (Video)," pp. 1-14, year 2010, as downloaded from https://timroot.com/how-to-perform-a-laser-iridotomy-video/.
AU Application # 2022211843 Office Action dated Sep. 27, 2023.
AU Application # 2021311097 Office Action dated Sep. 28, 2023.
U.S. Appl. No. 17/427,926 Office Action dated Oct. 17, 2023.
JP Application # 2021536316 Office Action dated Oct. 24, 2023.
JP Application # 2020561860 Office Action dated Oct. 31, 2023.

(56) References Cited

OTHER PUBLICATIONS

JP Application # 2021516473 Office Action dated Nov. 7, 2023.
SG Application # 11202010437T Office Action Dec. 5, 2023.
U.S. Appl. No. 17/735,153 Office Action dated Dec. 18, 2023.
U.S. Appl. No. 17/136,052 Office Action dated Dec. 22, 2023.
U.S. Appl. No. 17/427,926 Office Action dated Dec. 22, 2023.
International Application # PCT/IB2023/060104 Search Report Dec. 26, 2023.
U.S. Appl. No. 16/935,236 Office Action dated Nov. 7, 2022.
EP Application # 20769533.9 Search Report dated Nov. 8, 2022.
AU Application # 2020345067 Office Action dated Nov. 30, 2022.
CN Application # 201980070459X Office Action dated Dec. 23, 2022.
"Smart Selecta Duet—Your Smart Selection for Glaucoma Care," Product Brochure, pp. 1-6, The Lumenis Group of Companies, year 2018.
CN Application # 2020800163407 Office Action dated Feb. 4, 2023.
JP Application # 2020561860 Office Action dated Feb. 7, 2023.
Danielson et al., Fixed High-Energy versus Standard Titrated Energy Settings for Selective Laser Trabeculoplasty, Journal of Glaucoma Publish Ahead of Print, Wolters Kluwer Health, Inc., pp. 1-16, year 2023.
Radcliffe et al., "Energy Dose-Response in Selective Laser Trabeculoplasty: A Review," Journal of Glaucoma, vol. 31, pp. e49-e68, year 2022.
Gazzard, "A Brief Guide to Gonioscopy," Video Clip, Optometry today, pp. 1-2, May 21, 2015, as downloaded from https://www.youtube.com/watch?v=8yTTbHWxUik.
Alward et al., "Principles of Gonioscopy," Color Atlas of Gonioscopy, American Academy of Opthalmology, pp. 1-10, Nov. 8, 2017, as downloaded from https://www.aao.org/education/disease-review/principles-of-gonioscopy.
Nolan et al., "Gonioscopy skills and techniques," Community Eye Health Journal, vol. 34, No. 112, pp. 40-42, year 2021.
Breazzano et al., "Analysis of Schwalbe's Line (Limbal Smooth Zone) by Scanning Electron Microscopy and Optical Coherence Tomography in Human Eye Bank Eyes," Journal of Ophthalmic and Vision Research, vol. 8, issue 1, pp. 9-16, Jan. 2013.
Thorlabs, Inc., "CPS520—Collimated Laser Diode Module, 520 nm, 4.5 mW, Elliptical Beam, Ø11 mm," Product Details, pp. 1-1, years 1999-2023, as downloaded from https://www.thorlabs.com/thorproduct.cfm?partnumber=CPS520.
Prophotonix, "Green Laser Modules," Product Information, pp. 1-8, year 2024, as downloaded from https://www.prophotonix.com/led-and-laser-products/laser-modules/laser-modules-color/green-laser-modules/.
Idex Helath & Science LLC, "532 nm StopLine® single-notch filter," Product Details, pp. 1-2, year 2023 as downloaded from https://www.idex-hs.com/store/product-detail/nf03_532e_25/fl-009362?cat_id=products&node=individual_optical_filters.
Brackley et al., "Lecture: Using the Slit Lamp Microscope to Visualize the Ocular Structures," Video Clip, pp. 1-2, Sep. 17, 2022, as downloaded from https://www.youtube.com/watch?v=1E-sEhy9tBo.
Bruce et al., "Zoom in on Gonioscopy," Review of Optometry, pp. 1-8, Sep. 1, 2016, as downloaded from https://www.reviewofoptometry.com/article/zoom-in-on-gonioscopy.
AU Application # 2022211843 Office Action dated Jan. 8, 2024.
JP Application # 2022508451 Office Action dated Mar. 5, 2024.
AU Application # 2021369792 Office Action dated Mar. 21, 2024.
International Application # PCT/IB2023/061472 Search Report dated Feb. 29, 2024.
Nagar et al., "A randomised, prospective study comparing selective laser trabeculoplasty with latanoprost for the control of intraocular pressure in ocular hypertension and open angle glaucoma," British Journal of Ophthalmology, vol. 89, pp. 1413-1417, year 2005.
Hong et al., "Repeat Selective Laser Trabeculoplasty," Journal of Glaucoma, vol. 18, issue 3, pp. 180-183, Mar. 2009.
Goyal et al., "Effect of primary selective laser trabeculoplasty on tonographic outflow facility—a randomised clinical trial," British Journal of Ophthalmology, BMJ Publishing Group, vol. 94, issue 11, pp. 1-22, year 2010.
Franco et al., "Effect of Second SLT on IOP," Investigative Ophthalmology & Visual Science, vol. 48, pp. May 1-2, 2007.
Chen et al., "A Comparison between 90 degrees and 180 degrees Selective Laser Trabeculoplasty," Journal of Glaucoma, vol. 13, issue 1, p. 1, Feb. 2004.
Mequio et al., "Efficacy of Repeat Selective Laser Trabeculoplasty," Investigative Ophthalmology & Visual Science, vol. 48, p. 1, year 2007.
Grulkowski et al., "Anterior segment imaging with Spectral OCT system using a high-speed CMOS camera," Optics Express, vol. 17, No. 6, p. 4842-4858, year 2009.
Shields et al., "Noncontact Transscleral ND:YAG Cyclophotocoagulation: A Long-Term Follow-Up of 500 Patients," Transactions of the American Ophthalmological Society, vol. XCII, pp. 271-287, year 1994.
Liu et al., "Real-time visual analysis of microvascular blood flow for critical care," CVPR2015 paper as Open Access Version, provided by the Computer Vision Foundation, pp. 2217-2225, year 2015.
Desco et al., "Effect of prophylactic brimonidine on bleeding complications after cataract surgery," European Journal of Ophthalmology, vol. 15, pp. 228-232, year 2005.
Pasquali et al., "Dilute brimonidine to improve patient comfort and subconjunctival hemorrhage after LASIK," Journal of Refractive Surgery, vol. 29, pp. 469-475, year 2013.
Sacks et al., "Non-contact direct selective laser trabeculoplasty: light propagation analysis," Biomedical Optics Express, vol. 11, pp. 2889-2904, year 2020.
Kasuga et al., "Trabecular Meshwork Length in Men and Women by Histological Assessment," Current Eye Research, Early Online, pp. 1-5, Jun. 2012.
International Application # PCT/IB2020/058300 Search Report dated Dec. 27, 2020.
SensoMotoric Instruments GmbH (SMI), "SG 3000", Product Flyer, pp. 1-2, year 2010.
Ashik et al., "The precision of ophthalmic biometry using calipers," Canadian Journal of Ophthalmology, vol. 48, Issue 6, pp. 1-13, Dec. 2013.
Balalzsi, "Noncontact Thermal Mode Nd:YAG Laser Transscleral Cyclocoagulation in the Treatment of Glaucoma," Ophthalmology, vol. 98, pp. 1858-1863, year 1991.
Leung et al., "Anterior chamber angle imaging with optical coherence tomography," Eye, vol. 25, pp. 261-267, year 2011.
Tasman et al., "The Wills Eye Hospital Atlas of Clinical Ophthalmology," Lippincott Williams & Wilkins, p. 158, year 2001.
Gaasterland, "Laser Therapies: Iridotomy, Iridoplasty, and Trabeculoplasty," as appears in "The Glaucoma Book: A Practical Evidence-Based Approach to Patient Care," Springer, p. 722, year 2010.
Kara, "Bleeding in Retinal Images Using Image Processing", A Thesis submitted to the graduate school of applied sciences of Near East University, pp. 1-79, Nicosia, Larnaca, year 2019.
Navilas Operator Manual, Document Version 2.10, 2012 OD-OS GmbH, pp. 1-94, Sep. 2012.
Vogel et al., "Optical properties of human sclera, and their consequences for transscleral laser applications.", Lasers In Surgery and Medicine, vol. 11, pp. 331-340, 1991.
Geffen et al., "Transscleral Selective Laser Trabeculoplasty Without a Gonioscopy Lens", Journal of Glaucoma, Inc, vol. 26, No. 3, pp. 201-207, Mar. 2017.
Das et al., "Sclera Recognition—A Survey", 2nd IAPR Asian Conference on Pattern Recognition, pp. 1-5, Naha, Japan, Nov. 5-8, 2013.
Kaya et al., "Designing a Pattern Stabilization Method Using Scleral Blood Vessels for Laser Eye Surgery", International Conference on Pattern Recognition, pp. 698-701, Istanbul, Turkey, Aug. 23-26, 2010.
International Application # PCT/IB2019/055564 search report dated Oct. 10, 2019.

(56) References Cited

OTHER PUBLICATIONS

Arany, "Photobiomodulation therapy: Easy to do, but difficult to get right", LaserFocusWorld, pp. 1-6, Jul. 31, 2019 downloaded from www.laserfocusworld.com/lasers-sources/article/14037967/photobiomodulation-therapyeasy-to-do-but-difficult-to-get-right, pp. 22-24, year 2019.

Borzabadi-Farahani, "Effect of low-level laser irradiation on proliferation of human dental mesenchymal stem cells; a systemic review", Journal of Photochemistry and Photobiology B: Biology, vol. 162, pp. 577-582, Sep. 2016.

Ascott et al., "Trabecular Repopulation by Anterior Trabecular Meshwork Cells After Laser Trabeculoplasty", American Journal of Ophthalmology, vol. 107, issue 1, pp. 1-6, Jan. 1989.

Cao et al., "Peripheral Iridotomy," Medscape 25, pp. 1-12, Jun. 15, 2020.

Husain, "Laser Peripheral Iridotomy—Practical Points", YouTube presentation, p. 1, Sep. 28, 2016, downloaded from https://www.youtube.com/watch?=Azxzsv3lyls.

Sacks et al., U.S. Appl. No. 17/136,052, filed Dec. 29, 2020.

Smith et al., "Light scatter from the central human cornea", Journal "Eye", issue 4, pp. 584-588, year 1990.

Turati et al., "Patterned Laser Trabeculoplasty", Ophthalmic Surgery, Lasers and Imaging, vol. 41, No. 5, pp. 538-545, 2010.

Nozaki et al., "Patterned Laser Trabeculoplasty with PASCAL streamline 577", Investigative Ophthalmology & Visual Science, vol. 54, p. 1867, Jun. 2013.

Barkana et al., "Selective Laser Trabeculoplasty", Survey of Ophthalmology, vol. 52, No. 6, pp. 634-653, year 2007.

Ivandic et al., "Early Diagnosis of Ocular Hypertension Using a Low-Intensity Laser Irradiation Test", Photomedicine and Laser Surgery, vol. 00, No. 00, pp. 1-5, year 2009.

Acktar, "Magic Black Coatings", Product Information, pp. 1-6, year 2017.

Acktar, "Fractal Black Coating", Product Information, pp. 1-5, year 2017.

Cloudy Nights LLC, "Cloudy Nights—Equipment Discussions—ATM", Optics and DIY Forum, pp. 1-5, Feb. 15, 2015.

Defense Tech, "Anti-Laser Contact Lenses", Product Information, p. 1-1, Nov. 29, 2004.

IEC standard 60825-1, "Safety of Laser Products", Edition 1.2, pp. 1-122, years 2001-2008.

Laser Safety Industries, "Filter Specifications", pp. 1-5, year 2008.

Thorlabs, "Laser Safety Glasses", Product Information, p. 1, Nov. 3, 2014.

Surrey Nanosystems Ltd, "Vantablack", Data Sheet, pp. 1-4, Mar. 1, 2016.

International Application # PCT/IB2021/059821 Search Report dated Apr. 7, 2022.

U.S. Appl. No. 17/427,926 Office Action dated May 9, 2024.

EP Application # 19877990.2 Office Oction dated May 13, 2024.

EP Application # 24158977.9 Search Report dated May 15, 2024.

EP Applicatian # 21845437.9 Search Report dated Jun. 19, 2024.

JP Application # 2023217477 Office Action dated Jul. 9, 2024.

EP Application # 21885460.2 Search Report dated Aug. 26, 2024.

U.S. Appl. No. 17/427,926 Office Action dated Aug. 27, 2024.

EP Application # 19830473.5 Office Action dated Sep. 3, 2024.

Sridhar, "Anatomy of Cornea and Ocular Surface," Indidan Journal of Ophthalmology, vol. 66, issue 2, pp. 190-194, year 2018.

\* cited by examiner

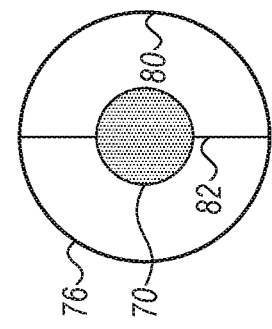
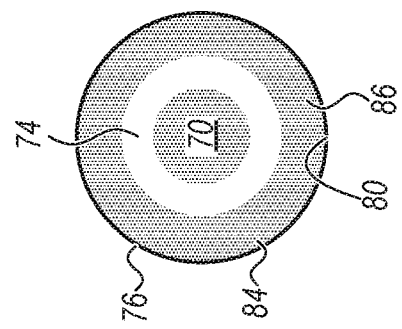
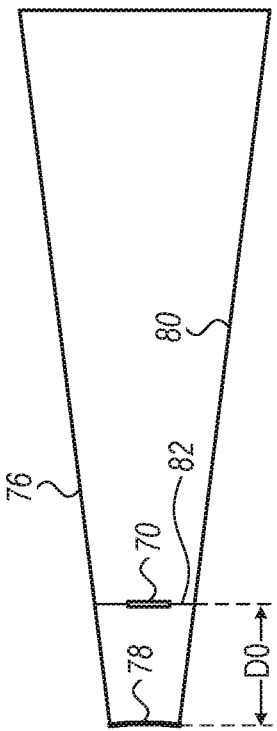
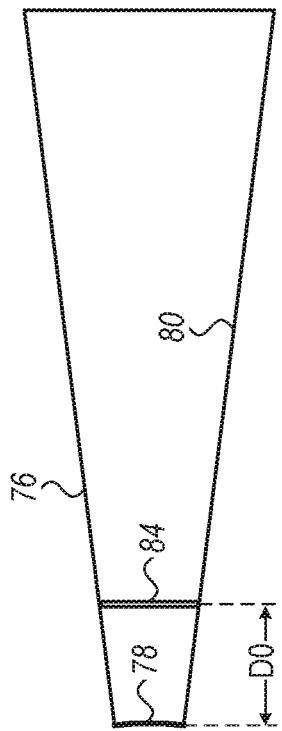
FIG. 3B
FIG. 4B
FIG. 3A
FIG. 4A

PROTECTION FOR DIRECT SELECTIVE LASER TRABECULOPLASTY

CROSS-REFERENCE TO RELATED APPLICATIONS

The present application claims the benefit of U.S. Provisional Appl. No. 62/751,629, entitled "DSLT Eye Protection," filed Oct. 28, 2018, whose disclosure is incorporated herein by reference.

FIELD OF THE INVENTION

The present invention relates to ophthalmological devices and methods for the treatment of glaucoma, ocular hypertension (OHT), and other diseases.

BACKGROUND

In a trabeculoplasty procedure, a radiation source, typically a laser, irradiates the trabecular meshwork in an eye of a patient with one or more treatment beams, thus lowering the intraocular pressure in the eye.

U.S. Pat. No. 4,848,894 describes a contact lens made either with a laser-reflecting or absorbing layer embedded in a transparent optical lens material, or formed as a layer on the convex side of such a material. The layer may be a Fabry-Perot reflector or a thin-film or holographically formed reflective or absorptive interference filter, or an absorbing layer.

U.S. Pat. No. 4,966,452 describes a contact lens for use in connection with transscleral cyclophotocoagulation. The lens has a planar entry surface and a frustoconically-shaped exit surface that contacts the sclera surrounding the cornea. The central portion of the lens is opaque to prevent stray laser light from entering the optical portion of the eye during laser application.

U.S. Pat. No. 6,948,815 describes individually marked contact lenses for protection of one's eyes from harmful radiation. Contact lenses are coated or treated to be absorptive or reflective to a preselected wavelength or wavelengths. The lenses contain one or more identification areas on each lens to demonstrate that the lenses are being worn and to indicate the proper applications with which the lenses should be used and/or the wavelengths for which the lens is protective. The identification area, which should be visible when worn to third parties and/or the person wearing the lenses, consists of markings such as colored bands or shaded areas in the region around the iris. Different colors or color patterns of the markings indicate which wavelengths the lens protects against. Other safety features may include fluorescent markers, added features and devices to facilitate placement and retention in the eye, pick-up or release.

U.S. Pat. No. 8,004,764 describes a filter and method for filtering an optical beam. One embodiment of the filter is an optical filter for filtering an incident light beam, comprising an optically effective material characterized by: a light transmittance of less than 1% for wavelengths below 420 nm; and a light transmittance for wavelengths complementary and near complementary to wavelengths below 420 nm that, combined with the transmittance for wavelengths below 420 nm, will yield a filtered light beam having a luminosity of about 90% and an excitation purity of 5% or less. The complementary wavelengths can be wavelengths above about 640 nm, wavelengths above about 660 nm, and/or wavelengths from about 540 nm to about 560 nm.

U.S. Pat. No. 9,480,599 describes an ophthalmic laser ablation system with various optional features, some especially suitable for non-penetrating filtration surgery on an eye. In one example, focusing of an ablation laser uses a movable lens coupled to a pair of converging light sources, which converge at the focal distance of the lens. In another example, laser ablation settings are selected for optimal ablation and minimal amount of thermal damage of a layer of percolating scleral tissue.

International Patent Application Publication WO/1998/022016 describes a combination of a scanning laser ophthalmoscope and a photocoagulator. The device includes a therapeutic laser source, optic-mechanical Maxwellian view coupling, Maxwellian view control, and real-time electronic registration of the therapeutic beam location.

SUMMARY OF THE INVENTION

There is provided, in accordance with some embodiments of the present invention, an apparatus including an optical unit. The optical unit includes a light source, one or more beam-directing elements, and a radiation source. The radiation source is configured to irradiate an eye of a patient with one or more treatment beams by emitting the treatment beams toward the beam-directing elements, while the eye fixates on the light source by virtue of the light source transmitting visible light. The apparatus further includes an optical filter configured to inhibit passage of the treatment beams, but not the visible light, therethrough, while interposing between the beam-directing elements and a pupil of the eye.

In some embodiments, the apparatus further includes an eye-stabilizing structure, the radiation source is configured to irradiate the eye by emitting the treatment beams through the structure, and the optical filter is coupled to the structure.

In some embodiments, a proximal end of the structure is configured to couple to optical unit.

In some embodiments, the optical filter is coupled to a distal end of the structure.

In some embodiments, the apparatus further includes a contact optic including the optical filter, and the contact optic is coupled to the distal end of the structure and is configured to contact the eye.

In some embodiments, a distal end of the structure is configured to contact the eye, and the optical filter is mounted to an inner wall of the structure.

In some embodiments, the optical filter is mounted between 0.5 and 20 mm from the distal end of the structure.

In some embodiments, the distal end of the structure includes a contact optic configured to contact the eye.

In some embodiments, the distal end of the structure includes a contact ring configured to contact the eye.

In some embodiments, the apparatus further includes one or more longitudinal elements extending between the inner wall of the structure and the optical filter, the optical filter being mounted to the inner wall via the longitudinal elements.

In some embodiments, an inner wall of the structure is configured to absorb the treatment beams.

In some embodiments, a treatment-beam wavelength of the treatment beams is between 200 and 11000 nm, and a visible-light wavelength of the visible light is between 350 and 850 nm.

In some embodiments, the optical filter is configured to inhibit the passage of the treatment beams by absorbing the treatment beams.

In some embodiments, the optical fit s configured to inhibit the passage of the treatment beams by reflecting the treatment beams.

In some embodiments, the optical filter includes an antireflective surface configured to reduce reflection of the treatment beams.

In some embodiments, the apparatus further includes an optic including:
the optical filter; and
a transparent portion that surrounds the optical filter and is transparent to the treatment beams.

In some embodiments,
the optical filter is a first optical filter, and
the optic further includes a second optical filter that surrounds the transparent portion and is configured to inhibit the passage of the treatment beams.

In some embodiments, the apparatus further includes a contact optic including the optical filter, and the contact optic is configured to contact the eye.

In some embodiments, a thickness of the contact optic is less than 2 mm.

In some embodiments, a diameter of the contact optic is less than 10 mm.

In some embodiments,
the optical unit includes a front face, and
the optical filter is coupled to the front face.

In some embodiments,
the front face includes an exit window,
the light source is configured to transmit the visible tight, and the radiation source is configured to emit the treatment beams, through the exit window, and
the optical filter overlays the exit window.

In some embodiments,
the front face includes an exit window,
the light source is configured to transmit the visible light, and the radiation source is configured to emit the treatment beams, through the exit window, and
the optical filter is embedded within the exit window.

In some embodiments, the apparatus further includes a longitudinal element extending between the front face and the optical filter, the optical filter being coupled to the front face via the longitudinal element.

In some embodiments,
the front face includes an exit window,
the light source is configured to transmit the visible light, and the radiation source is configured to emit the treatment beams, through the exit window, and
the longitudinal element extends between the exit window and the optical filter.

There is further provided, in accordance with some embodiments of the present invention, a method including interposing an optical filter between one or more beam-directing elements and a pupil of an eye of a patient. The method further includes, while the optical filter interposes between the beam-directing elements and the pupil, using a light source, transmitting visible light through the optical filter and, while the eye fixates on the light source by virtue of the light source transmitting the visible light, irradiating the eye with one or more treatment beams by emitting the treatment beams toward the beam-directing elements, the optical filter being configured to inhibit passage of the treatment beams therethrough.

In some embodiments, the optical filter belongs to a contact optic, and interposing the optical filter includes interposing the optical filter by contacting the eye with the contact optic.

There is further provided, in accordance with some embodiments of the present invention, a system including a camera, configured to acquire an image of an eye of a patient, a radiation source, and a controller. The controller is configured to identify a static region in a field of view of the camera that, in the image, is outside a limbus of the eye, and to treat one or more target regions of the eye, by, for each target region, ascertaining that the target region is not within the static region, and in response to the ascertaining, causing the radiation source to irradiate the target region.

There is further provided, in accordance with some embodiments of the present invention, a method including, using a camera, acquiring an image of an eye of a patient. The method further includes identifying a static region in a field of view of the camera that, in the image, is outside a limbus of the eye. The method further includes treating one or more target regions of the eye, by, for each target region, ascertaining that the target region is not within the static region, and in response to the ascertaining, irradiating the target region.

There is further provided, in accordance with some embodiments of the present invention, an apparatus including an optical unit. The optical unit ludes a light source, configured to transmit visible light, one or more beam-directing elements, and a radiation source, configured to irradiate a first eye of a patient with one or more treatment beams by emitting the treatment beams toward the beam-directing elements such that the beam-directing elements direct the treatment beams along an optical path to the first eye. The apparatus further includes an optical filter configured to inhibit the visible light and the treatment beams from reaching a pupil of the first eye. The light source is displaced from the optical path towards a second eye of the patient, and the radiation source is configured to irradiate the first eye while the second eye fixates on the light source by virtue of the light source transmitting the visible light.

In some embodiments, the light source is displaced from the optical path by 18-44 mm.

There is further provided, in accordance with some embodiments of the present invention, a method, including interposing an optical filter, which is opaque to visible light transmitted by a light source and to treatment beams emitted by a radiation source, between (i) one or more beam-directing elements and (ii) a pupil of a first eye of a patient. The method further includes, while a second eye of the patient fixates on the light source by virtue of the light source transmitting the visible light, using the radiation source, irradiating the first eye with the treatment beams by emitting the treatment beams toward the beam-directing elements.

In some embodiments, the beam-directing elements direct the treatment beams along an optical path to the first eye, and the method further includes, prior to irradiating the first eye, displacing the light source from the optical path towards the second eye.

The present invention will be more fully understood from the following detailed description of embodiments thereof, taken together with the drawings, in which:

BRIEF DESCRIPTION OF THE DRAWINGS

FIGS. 3A-B are schematic illustrations of an eye-stabilizing structure as viewed from the side and from the front, respectively, in accordance with some embodiments of the present invention;

FIGS. 4A-B are schematic illustrations of an eye-stabilizing structure as viewed from the side and from the front, respectively, in accordance with some embodiments of the present invention;

DETAILED DESCRIPTION OF EMBODIMENTS

Overview

Figure 1:
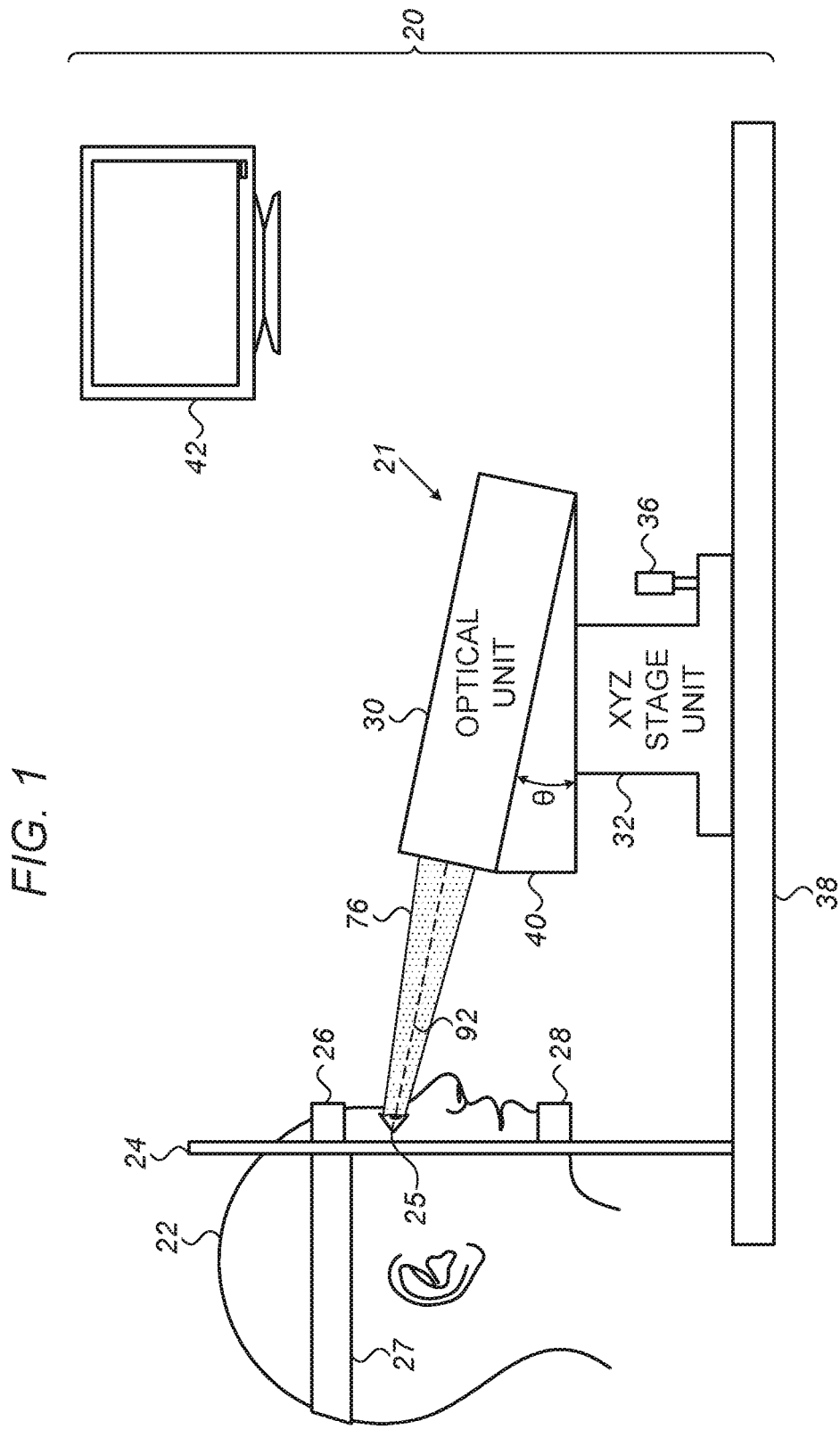
FIG. 1 is a schematic illustration of a system for performing a trabeculoplasty procedure, in accordance with some embodiments of the present invention.

Embodiments of the present invention provide an automated trabeculoplasty device configured to perform a trabeculoplasty procedure on an eye safely and efficiently. The trabeculoplasty device comprises a controller and an optical unit, which comprises a radiation source (typically a laser), a camera and one or more illumination sources for imaging, one or more beam-directing elements, and a light source. By transmitting (i.e., emitting or reflecting) visible light, the light source functions as a fixation target for the eye. While the eye fixates on the light source, the controller, in response to feedback from the camera, causes the beam-directing elements to direct beams of radiation, which are emitted by the radiation source, toward targeted regions of the eye, which are typically located in the vicinity of the limbus of the eye.

Embodiments of the present invention further provide an optical filter that is opaque to the treatment beams, but not to the visible light transmitted by the light source. By interposing between the optical unit and the pupil of the eye, the optical filter protects the retina of the eye from any stray radiation beams without inhibiting the eye from fixating on the fixation target.

In some embodiments, the optical filter belongs to a contact optic, which is worn in the eye without being held in place by any other element of the system. In other embodiments, the optical filter is mounted within or at the end of an eye-stabilizing structure, such as a hollow frustum-shaped structure, extending between the optical unit and the eye. In addition to supporting the optical filter, the eye-stabilizing structure may perform additional functions; for example, the eye-stabilizing structure may hold the eye open, stabilize the eye, and/or absorb any misaimed treatment beams. In yet other embodiments, the optical filter overlays the exit window of the optical unit, is embedded within the exit window, or is otherwise coupled to the optical unit.

In some embodiments, the peripheral portion of the eye lying outside the target regions is also protected. This protection may be provided by an additional (physical) optical filter. Alternatively or additionally, this protection may be provided by a virtual fitter, in that the controller may identify a region in the camera's FOV in which the peripheral portion of the eye is located, and then inhibit the treatment beams from being fired at this region.

Although the present description focuses mainly on trabeculoplasty procedures, the techniques described herein may also be applied to automatic photocoagulation procedures, iridotomy procedures, corneal procedures, capsulectomy procedures, lens removals, or any other relevant ophthalmological procedures. The target of the radiation may include the trabecular meshwork and/or any other suitable portion of the eye. Embodiments of the present invention may be used to treat glaucoma, ocular hypertension (OHT), and other diseases.

It is noted that in the context of the present application, including the claims, an optical element is said to be "opaque" to visible light transmitted therethrough if the element attenuates the light (by reflection and/or absorption) to an intensity that is less than the minimum intensity at which an average human eye is able to perceive the light. For other types of radiation, the optical element is said to be opaque to the radiation if the element attenuates the radiation (by reflection and/or absorption) to an intensity that is less than the maximum permissible exposure (MPE) value for the radiation as defined in any relevant standard, such as the International Electrotechnical Commission (IEC) 60825 standard.

Conversely, in the context of the present application, including the claims, an optical element is said to be "transparent" to radiation if the element is not opaque to the radiation.

System Description

Figure 2:
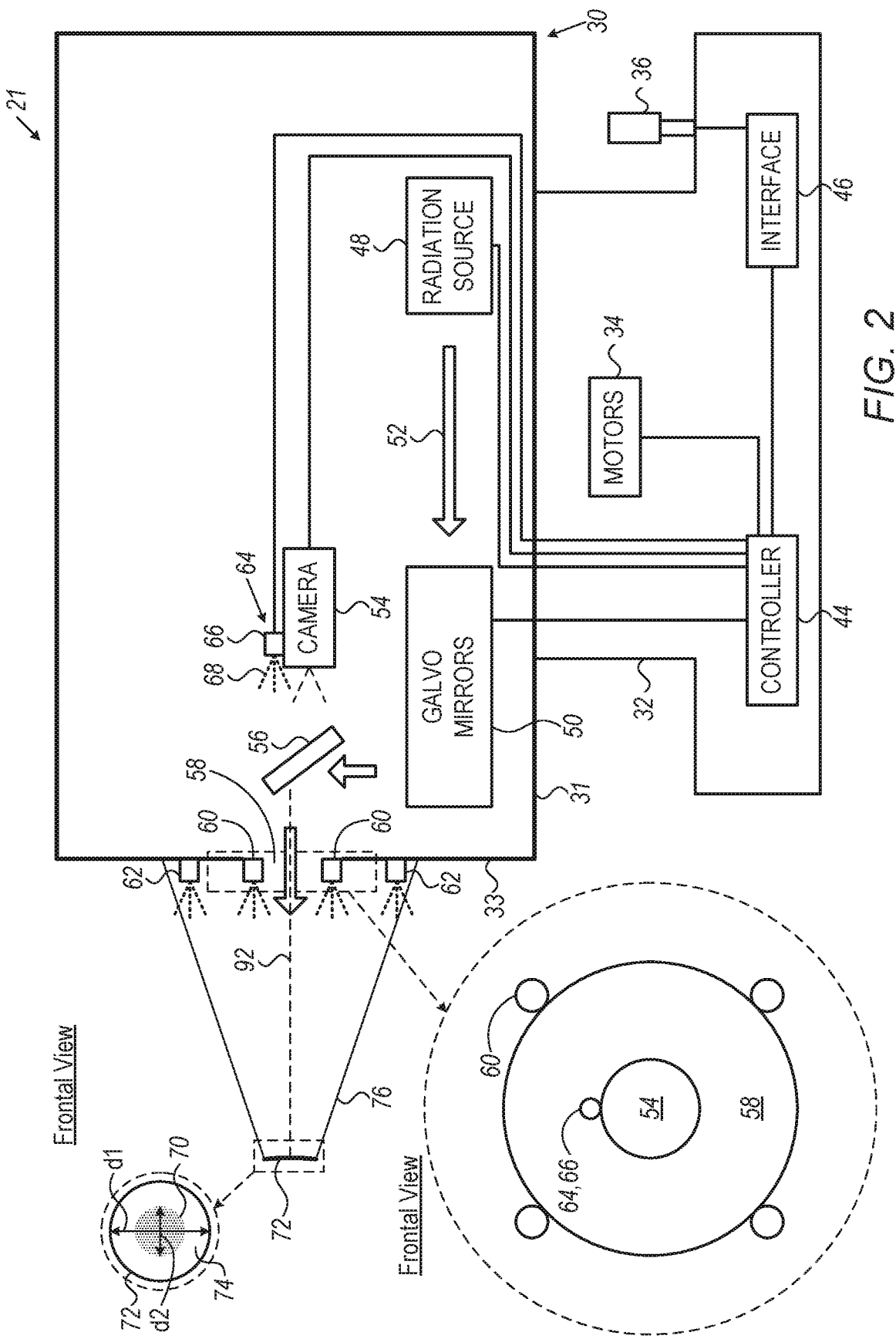
FIG. 2 is a schematic illustration of a trabeculoplasty device, in accordance with some embodiments of the present invention.

Reference is initially made to FIG. 1, which is a schematic illustration of a system 20, comprising a trabeculoplasty device 21, for performing a trabeculoplasty procedure, in accordance with some embodiments of the present invention. Reference is further made to FIG. 2, which is a schematic illustration of trabeculoplasty device 21, in accordance with some embodiments of the present invention.

Trabeculoplasty device 21 comprises an optical unit 30 and a controller 44. Optical unit 30 comprises one or more beam-directing elements, comprising, for example, one or more galvo mirrors 50, which may be referred to collectively as a "galvo scanner," and/or a beam combiner 56. Optical unit 30 further comprises a radiation source 48, which is configured to irradiate an eye 25 of a patient 22 with one or more treatment beams 52 by emitting the treatment beams toward the beam-directing elements such that the beams are directed by the beam-directing elements toward the eye.

More specifically, before the emission of each treatment beam 52 from radiation source 48, or while the beam is being emitted, controller 44 aims the beam-directing elements at the desired target region on eye 25 such that the beam is directed, by the beam-directing elements, toward the target region. For example, the beam may be deflected by galvo mirrors 50 toward beam combiner 56, and then deflected by the beam combiner such that the beam impinges on the target region. (Since each treatment beam impinges on the eye with a non-infinitesimal spot size, the present application generally describes each beam as impinging on a "region" of the eye, whose area is a function of the spot size, rather than impinging at a "point" on the eye.) The beam thus follows an optical path 92, which extends from the most downstream of the beam-directing elements—such as beam combiner 56—to eye 25. (In practice, the respective paths of the beams vary slightly from each other due to the small distances between the target regions; however, given that this variation is very slight, the present description refers to a single optical path 92 followed by all the treatment beams.)

Typically, the radiation source comprises a laser, such as an Ekspla™ NL204-0.5K-SH laser. The laser may be modified to include an attenuator, an energy meter, and/or a mechanical shutter. Alternatively or additionally to a laser, the radiation source may comprise any other suitable emitter.

In some embodiments, the treatment beams comprise visible light. Alternatively or additionally, the treatment beams may comprise non-visible radiation, such as microwave radiation, infrared radiation, X-ray radiation, gamma radiation, or ultraviolet radiation. Typically, the wavelength of the treatment beams is between 200 and 11000 nm, e.g., 500-850 nm, such as 520-540 nm, e.g., 532 nm. Each treatment beam 52 may have an elliptical (e.g., a circular) shape, a square shape, or any other suitable shape.

Optical unit 30 further comprises a camera 54. As shown n FIG. 2, camera 54 is typically aligned, at least approximately, with optical path 92; for example, the angle between optical path 92 and a hypothetical line extending from eye 25 to the camera may be less than 15 degrees. In some embodiments, the camera is positioned behind beam combiner 56, such that the camera receives light via the beam combiner.

Before the procedure, camera 54 acquires at least one image of eye 25. Based on the image, controller 44 and/or a user of the system, such as an ophthalmologist or another physician, may define and/or modify the target regions of the eye that are to be irradiated. Alternatively or additionally, based on the image, controller 44 may define one or more virtual filters, as further described below with reference to FIG. 8. Subsequently, during the procedure, camera 54 may acquire multiple images of the patient's eye at a relatively high frequency. Controller 44 may process these images and, in response thereto, control radiation source 48 and the beam-directing elements so as to irradiate the target regions of the eye.

Optical unit 30 further comprises a light source 66, which is aligned, at least approximately, with optical path 92. For example, the angle between optical path 92 and a hypothetical line extending from the end of path 92 on eye 25 to light source 66 may be less than 20 degrees, such as less than 10 degrees. Light source 66 is configured to function as a fixation target 64 by transmitting visible light 68. (It is noted that visible light 68 may also be described as a "fixation beam" or as "fixation light.")

In particular, prior to the procedure, patient 22 is instructed to fixate eye 25 on light source 66. Subsequently, during the procedure, by virtue of light source 66 transmitting visible light 68, eye 25 fixates on the light source, such that the eye's line-of-sight is approximately coincident with optical path 92 (due to the light source being approximately aligned with the optical path) and the eye is relatively stable. While the eye fixates on the light source, the radiation source irradiates the eye with treatment beams 52. Light source 66 may also help orient the eye while an aiming beam is swept across the eye prior to the procedure, as further described below with reference to FIG. 8.

In some embodiments, light source 66 comprises a light emitter, such as a light emitting diode (LED). In other embodiments, the light source comprises a reflector configured to reflect light emitted from a light emitter.

Typically, the wavelength of visible light 68, which may be higher or lower than that of the treatment beams, is between 350 and 850 nm. For example, visible light 68 may be red, with a wavelength of 600-700 nm, while the treatment beams may be green, with a wavelength of 527-537 nm.

Typically, the optical unit comprises an optical bench, and at least some of the aforementioned optical components belonging to the optical unit, such as the radiation source, the galvo mirrors, and the beam combiner, are coupled to the optical bench. Typically, the optical unit further comprises a front face 33, through which the treatment beams and visible tight 68 pass. For example, optical unit 30 may comprise an encasement 31, which at least partially encases the optical bench and comprises front face 33. (Encasement 31 may be made of a plastic, a metal, and/or any other suitable material.) Alternatively, front face 33 may be attached to, or may be an integral part of, the optical bench.

Figure 5:
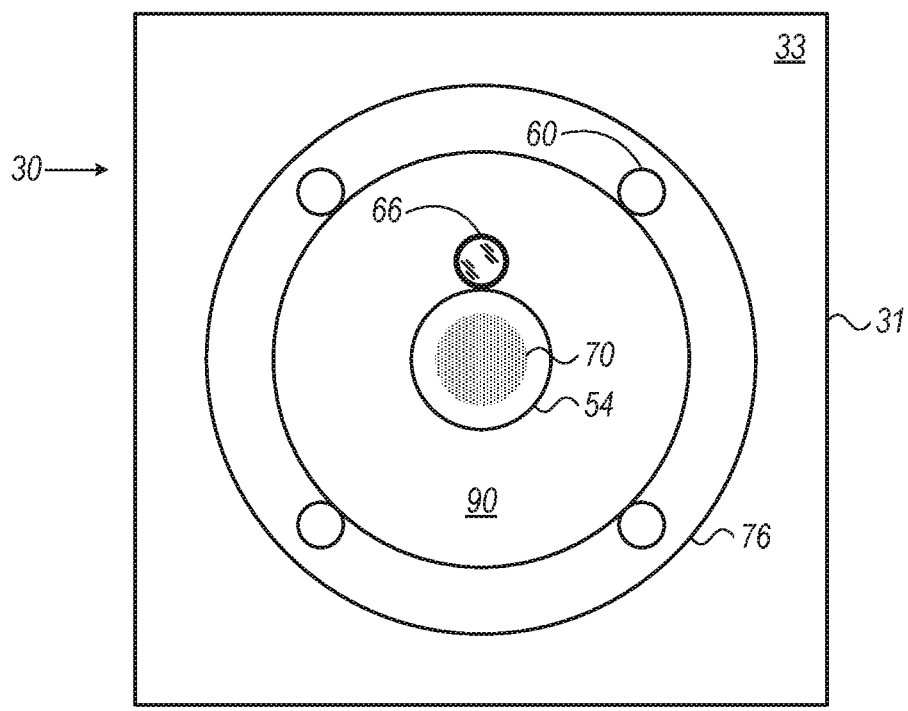
FIGS. 5-6 are schematic illustrations of an optical filter coupled to an optical unit, in accordance with some embodiments of the present invention.

In some embodiments, front face 33 is shaped to define an opening 58, through which the treatment beams and visible light 68 pass. In other embodiments, as shown in FIG. 5 (described below), the front face comprises an exit window in lieu of opening 58, such that visible light 68 and treatment beams 52 pass through the exit window. The exit window may be made of a plastic, a glass, or any other suitable material.

Typically, optical unit 30 further comprises one or more illumination sources 60 comprising, for example, one or more LEDs, such as white-light or infrared LEDs. For example, the optical unit may comprise a ring of LEDs surrounding opening 58. In such embodiments, controller 44 may cause illumination sources 60 to intermittently flash light at the eye, as described in International Patent Application PCT/IB2019/055564, whose disclosure is incorporated herein by reference. This flashing may facilitate the imaging performed by the camera, and may further help constrict the pupil of the eye. (For ease of illustration, the electrical connection between controller 44 and illumination sources 60 is not shown explicitly in FIG. 2.) In some embodiments, illumination sources 60 are coupled to front face 33, as shown in FIG. 2.

To facilitate positioning the optical unit, the optical unit may comprise a plurality of beam emitters 62 (comprising, for example, respective laser diodes), which are configured to shine a plurality of triangulating range-finding beams on the eye, e.g., as described in International Patent Application PCT/IB2019/055564. In some embodiments, beam emitters 62 are coupled to front face 33, as shown in FIG. 2. In other embodiments, beam emitters 62 are coupled directly to the optical bench.

Optical unit 30 is mounted onto an XYZ stage unit 32, which is controlled by a control mechanism 36, such as a joystick. Using control mechanism 36, the user of system 20 may position the optical unit (e.g., by adjusting the distance of the optical unit from the eye) prior to treating the eye. In some embodiments, XYZ stage unit 32 comprises locking elements configured to inhibit motion of the stage unit following the positioning of the stage unit.

In some embodiments, XYZ stage unit 32 comprises one or more motors 34, and control mechanism 36 is connected to interface circuitry 46. As the user manipulates the control mechanism, interface circuitry 46 translates this activity into appropriate electronic signals, and outputs these signals to controller 44. In response to the signals, the controller controls the motors of the XYZ stage unit.

In other embodiments, XYZ stage unit 32 is controlled manually by manipulating the control mechanism. In such embodiments, the XYZ stage unit may comprise a set of gears instead of motors 34.

System 20 further comprises a headrest 24, comprising a forehead rest 26 and a chinrest 28. During the trabeculoplasty procedure, patient 22 presses his forehead against forehead rest 26 while resting his chin on chinrest 28. In some embodiments, headrest 24 further comprises an immobilization strap 27, configured to secure the patient's head from behind and thus keep the patient's head pressed against the headrest.

In some embodiments, as shown in FIG. 1, headrest 24 and XYZ stage unit 32 are both mounted onto a surface 38, such as a tray or tabletop. (In some such embodiments, the headrest is L-shaped, and is attached to the side, rather than the top, of surface 38.) In other embodiments, the XYZ stage unit is mounted onto surface 38, and the headrest is attached to the XYZ stage unit.

Typically, as shown in FIG. 1, while irradiating the patient's eye, the optical unit is directed obliquely upward toward the eye while the eye gazes obliquely downward toward the optical unit, such that optical path 92 is oblique. For example, the optical path may be oriented at an angle θ of between five and twenty degrees with respect to the horizontal. Advantageously, this orientation reduces occlusion of the patient's eye by the patient's upper eyelid and associated anatomy.

In some embodiments, as shown in FIG. 1, the oblique orientation of the optical path is achieved by virtue of the optical unit being mounted on a wedge 40, which is mounted on the XYZ stage unit. In other words, the optical unit is mounted onto the XYZ stage unit via wedge 40. (Wedge 40 is omitted from FIG. 2.)

System 20 further comprises a monitor 42, configured to display the images of the eye acquired by the camera. Monitor 42 may be attached to optical unit 30 or disposed at any other suitable location, such as on surface 38 next to device 21. In some embodiments, monitor 42 comprises a touch screen, and the user inputs commands to the system via the touch screen. Alternatively or additionally, system 20 may comprise any other suitable input devices, such as a keyboard or a mouse, which may be used by the user.

In some embodiments, monitor 42 is connected directly to controller 44 over a wired or wireless communication interface. In other embodiments, monitor 42 is connected to controller 44 via an external processor, such as a processor belonging to a standard desktop computer.

In some embodiments, as shown in FIG. 2, controller 44 is disposed within XYZ stage unit 32. In other embodiments, controller 44 is disposed externally to the XYZ stage unit. Alternatively or additionally, the controller may cooperatively perform at least some of the functionality described herein with another, external processor.

In some embodiments, at least some of the functionality of controller 44, as described herein, is implemented in hardware, e.g., using one or more Application-Specific Integrated Circuits (ASICs) or Field-Programmable Gate Arrays (FPGAs). Alternatively or additionally, controller 44 may perform at least some of the functionality described herein by executing software and/or firmware code. For example, controller 44 may comprise a central processing unit (CPU) and random access memory (RAM). Program code, including software programs, and/or data may be loaded into the RAM for execution and processing by the CPU. The program code and/or data may be downloaded to the controller in electronic form, over a network, for example. Alternatively or additionally, the program code and/or data may be provided and/or stored on non-transitory tangible media, such as magnetic, optical, or electronic memory. Such program code and/or data, when provided to the controller, produce a machine or special-purpose computer, configured to perform the tasks described herein. In some embodiments, the controller comprises a system on module (SOM), such as the Varisite™ DART-MX8M.

The Optical Filter

As shown in FIG. 2, trabeculoplasty device 21 further comprises an optical filter 70, which is opaque to the treatment beams but not to visible light 68. (In some embodiments, the optical filter is also transparent to the light emitted by illumination sources 60 and/or the light emitted by beam emitters 62.) Optical filter 70 is configured to inhibit passage of the treatment beams, but not visible light 68, therethrough, while interposing between the beam-directing elements and the pupil of eye 25. (For ease of description, this act of interposing is referred to as "covering" the pupil.) Thus, the optical filter protects the retina of the eye while allowing the eye to fixate on fixation target 64. Typically, the optical filter is elliptical, e.g., circular. The optical filter may attenuate the treatment beams with an optical density (OD) that is between one and six, or even greater than six.

In some embodiments, optical filter 70 inhibits the passage of the treatment beams by absorbing the treatment beams. For example, optical filter 70 may comprise an absorptive plastic and/or an absorptive glass, such as a material used in the Thorlabs LG14 laser safety glasses or the Laser Safety Industries 35-235 laser safety glasses.

In such embodiments, the optical filter may comprise an anti-reflective surface configured to reduce reflection of the treatment beams. For example, the optical filter may comprise an absorptive material having a surface that is etched (e.g., subwavelength surface textured) or coated (e.g., with a dielectric coating) to reduce reflections therefrom. (The aforementioned coating may comprise a single layer or multiple layers.) In some embodiments, both surfaces of the optical filter are anti-reflective; the front anti-reflective surface, which faces the optical unit, protects the user of the system from any primary reflections, while the back anti-reflective surface protects the eye from any secondary reflections. In other embodiments, only one the surfaces, such as the front surface, is anti-reflective.

Alternatively or additionally to absorbing the treatment beams, the optical filter may inhibit the passage of the treatment beams by reflecting the treatment beams. For example, the optical filter may comprise a piece of transparent material (such as plastic or glass, for example) coated with a thin-film or broadband reflective coating. Such a coating may be applied to the front surface of the piece of material, which faces the optical unit, and/or the back surface, which faces the eye.

In some embodiments, the trabeculoplasty device further comprises a contact optic 72, which comprises the optical filter and is configured to contact the eye. (Typically, contact optic 72 is elliptical, e.g., circular.) During the procedure, contact optic 72 contacts eye 25, with optical filter 70 covering the pupil of the eye. (It is noted that in the context of the present application, including the claims, the term "contact" may include contact via an optical coupling fluid or a gel.) Typically, the contact optic is curved, so as to conform to the shape of the eyeball of eye 25. In some embodiments, the thickness of the contact optic is less than 2 mm, such that the contact optic may be worn in the eye without being held in place.

In some embodiments, contact optic 72 comprises the optical filter along with a transparent portion 74, which surrounds the optical filter and is transparent to the treatment beams and to visible light 68. (Typically, transparent portion 74 is annular-elliptical, e.g., annular-circular.) In such embodiments, the diameter d1 of the contact optic is typically 12-17 mm, with the diameter d2 of the optical filter typically being less than 10 mm. During the procedure, optical filter 70 covers the pupil of the eye (and, typically, at least part of the cornea surrounding the pupil), while transparent portion 74 covers the targeted vicinity of the limbus. Hence, the vicinity of the limbus may be irradiated by the treatment beams and may also be imaged by camera 54.

For example, contact optic 72 may comprise a transparent optic having a central portion coated with a reflective coating, which constitutes the optical filter, along with an uncoated peripheral portion. Alternatively, for embodiments in which the optical filter comprises an absorptive material, the optical filter may be embedded in the center of a transparent optic. Such embedding may be performed using diffusion bonding, welding, soldering, or an adhesive.

In some embodiments, the contact optic further comprises another optical filter that surrounds the transparent portion and inhibits passage of the treatment beams therethrough, as described below with reference to FIGS. 4A-B.

In other embodiments, the contact optic comprises the optical filter without comprising transparent portion 74. In such embodiments, diameter d1 (which is equal to diameter d2 due to the absence of transparent portion 74) is typically less than 10 mm, such that, during the procedure, the limbus and/or sclera of the eye are exposed. Although corrective contact lenses typically have a larger diameter so as not to discomfort the wearer, the inventors have realized that contact optic 72 is unlikely to discomfort the patient despite its small size, particularly if anesthetic eye drops are applied to the eye before the contact optic is placed in the eye.

In some embodiments, the trabeculoplasty device further comprises an eye-stabilizing structure 76, through which the various types of radiation described herein pass. Typically, the length of structure 76 is between 10 and 70 mm.

In such embodiments, optical filter 70 is typically coupled to structure 76. For example, as shown in FIG. 2, contact optic 72 may be coupled to the distal end of the structure, such that optical filter 70 is coupled to the distal end of structure 76 by virtue of the contact optic comprising the optical filter. (In such embodiments, the thickness of the contact optic is typically greater than 2 mm; for example, the thickness may be between 3 and 20 mm.) For example, the edge of the contact optic may be coupled to the distal end of the structure using a mechanical attachment mechanism, such as a screw, and/or any suitable adhesive. Alternatively, optical filter 70 may be coupled to structure 76 in other ways, as further described below with reference to FIGS. 3A-B and 4A-B.

Typically, structure 76 is hollow, such that the radiation described herein passes through air within the structure. For example, structure 76 may comprise a frustum-shaped or cylindrically-shaped tube, which may be made from metal, glass, or any other suitable material. In some such embodiments, the structure comprises a continuous wall. In other such embodiments, structure 76 is shaped to define one or more openings. For example, structure 76 may comprise a wire structure, such as a wire mesh. As further described below with reference to FIG. 8, an advantage of such embodiments is that the user may view the eye through the openings.

In other embodiments, structure 76 comprises a frustum-shaped or cylindrically-shaped transparent piece of material (e.g., glass), such that the radiation passes through the material.

Structure 76 typically provides several advantages, alternatively or additionally to holding optical filter 70. For example, as shown in FIG. 1, the distal end of structure 76 may retract the eyelids of eye 25. Additionally, the distal end of the structure may stabilize the eye, i.e., inhibit the eye from moving. Furthermore, structure 76 may facilitate placing the optical unit at the correct distance from the patient. Moreover, the inner and/or outer surface of structure 76 may be configured to absorb any misaimed treatment beams or scattered light, and/or to block any external light from interfering with the camera. For example, the inner and/or outer surface of the structure may comprise black flat paint, black flocked paper, or Vantablack.

In some embodiments, as shown in FIGS. 1-2, the proximal end of the structure is configured to couple to the optical unit, e.g., via a spring. In such embodiments, the trabeculoplasty device may further comprise a pressure sensor coupled to structure 76 and configured to measure the pressure applied to the structure. Based on the pressure measurement, the user may position the optical unit such that the pressure applied to the structure, which is equivalent to the pressure applied to the eye, is within a predefined range suitable for stabilizing the eye without hurting the patient. In other embodiments, the structure is not coupled to the optical unit, but rather, is held by the user of system 20 during the procedure.

In some embodiments, structure 76 is disposable, and a different respective structure is used for each patient.

As noted above, the optical unit may comprise an exit window in lieu of opening 58. In such embodiments, as further described below with reference to FIG. 5, the optical filter may overlay, or may be embedded within, the exit window.

As further described below with reference to FIG. 8, during the procedure, controller 44 may process images of the eye to calculate the position of each of the target regions. In some embodiments, the controller identifies contact optic 72 in each of the images, and verifies that the contact optic is in the correct location relative to the eye. Optionally, the controller may also calculate the position of the target region with reference to the position of the contact optic.

In some embodiments, to facilitate identifying the contact optic, the contact optic is opaque to wavelengths to which the camera is sensitive. For example, for embodiments in which the wavelength of the fixation light is between 600 and 700 nm, the camera may be sensitive only to wavelengths below 600 nm, and the contact optic may be opaque to wavelengths below 600 nm.

In other embodiments, the controller does not identify the contact optic in any of the images.

In some embodiments—particularly if structure 76 is not used—a finger, a speculum, or another tool may be used to retract one or both of the eyelids of eye 25.

It is emphasized that the configuration of device 21 shown in FIG. 2 is provided by way of example only. Moreover, alternatively or additionally to the components shown in FIG. 2, device 21 may comprise any suitable components.

Reference is now made to FIGS. 3A-B, which are schematic illustrations of structure 76 as viewed from the side and from the front, respectively, in accordance with some embodiments of the present invention. Reference is further made to FIGS. 4A-B, which are also schematic illustrations of structure 76 as viewed from the side and from the front, respectively, in accordance with some embodiments of the present invention.

In some embodiments, the optical filter is situated proximally to the distal end of eye-stabilizing structure 76, such that the distal end of the eye-stabilizing structure, but not the optical filter, contacts the eye. For example, as shown in FIGS. 3A and 4A, the optical filter may be mounted to the inner wall 80 of structure 76, e.g., at a distance D0 of 0.5-20 mm from the distal end of the structure. In such embodiments, diameter d2 of the optical filter (FIG. 2) is matched to distance D0, such that the optical filter covers the pupil without covering the targeted regions of the eye. In other words, for a smaller D0, d2 is made larger, and vice versa.

In some embodiments, as shown in FIGS. 3A-B, the optical filter is mounted to inner wall 80 via one or more longitudinal elements 82, such as stiff wires or posts, extending between the inner wall and the optical filter.

In other embodiments, as shown in FIGS. 4A-B, the trabeculoplasty device comprises an optic 84, which comprises optical filter 70 along with transparent portion 74. In such embodiments, the edge of optic 84 may be coupled to inner wall 80 using a mechanical attachment mechanism, such as a screw, and/or any suitable adhesive. (Since optic 84 does not need to conform to the shape of the eye, optic 84 is typically not curved.)

In some embodiments, optic 84 further comprises another optical filter 86 that surrounds transparent portion 74 and is configured to inhibit the passage of the treatment beams. (Typically, optical filter 86 is annular-elliptical, e.g., annular-circular.) For example, optical filter 86 may comprise an absorptive material and/or a thin-film reflective coating, such that optical filter 86 absorbs and/or reflects the treatment beams. Typically, optical filter 86 comprises the same materials as does optical filter 70 and/or is etched in the same way as is optical filter 70.

For embodiments in which the optical filter is situated proximally to the distal end of the eye-stabilizing structure, the distal end of the structure may comprise a contact optic 78 configured to help stabilize the eye by contacting the eye. Typically, contact optic 78, or at least the portion of the contact optic that covers the treated vicinity of the limbus, is transparent to the treatment beams and to visible light. Typically, the diameter of contact optic 78 is between 12 and 17 mm. (It is noted that the view of the eye-stabilizing structure in each of FIGS. 3B and 4B corresponds to the view seen through contact optic 78.)

In some embodiments, contact optic 78 is shaped to define an opening, and the trabeculoplasty device further comprises (i) a suction-applying device, such as a pump, and (ii) a tube having a proximal end connected to the suction-applying device and a distal end passing through the opening. In such embodiments, the suction-applying device may apply a suction force through the tube, thus helping the contact optic to stabilize the eye.

Alternatively or additionally to contact optic 78, the distal end of the structure may comprise a contact ring configured to help stabilize the eye by contacting the eye. Typically, the contact ring contacts the eye outside of, and sufficiently far from (e.g., at least 2 mm from), the limbus, such that the portion of the eye targeted by the treatment beams, which typically includes the limbus and/or part of the sclera, is exposed to the treatment beams and to the camera. For example, the diameter of the contact ring may be between 14 and 18 mm. In some embodiments, the contact ring does not contact the eye continuously, but rather, only over several (e.g., between three and ten) points of contact.

In some embodiments, to facilitate stabilizing the eye, suction may be applied through the contact ring, as described above for contact optic 78. In addition to stabilizing the eye, the contact ring may retract the eyelids of the eye.

Figure 6:
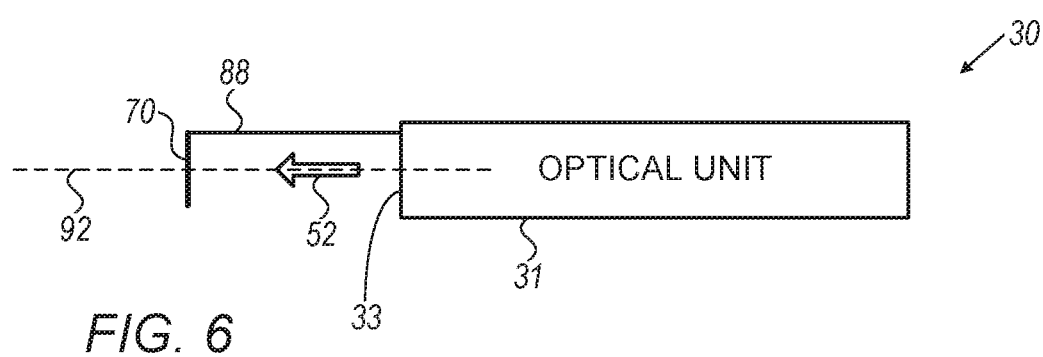

Reference is now made to FIGS. 5-6, which are schematic illustrations of optical filter 70 coupled to optical unit 30, in accordance with some embodiments of the present invention.

In some embodiments, optical filter 70 is coupled to the optical unit.

For example, as shown in the frontal view of the optical unit in FIG. 5, the optical filter may overlay, or may be embedded within, an exit window 90 belonging to front face 33. For example, the optical filter may comprise a thin-film reflective coating that coats exit window 90. (To avoid any confusion, it is noted that the frontal view of the optical unit shown in FIG. 5 is not the view typically seen by the patient during the procedure; in the latter view, optical filter 70 fills the patient's field of view, given that the optical filter typically covers the patient's entire pupil.)

As another example, as shown in FIG. 6, a longitudinal element 88, such as a stiff wire or a post, may extend between the front face and the optical filter, and the optical filter may be coupled to the front face via longitudinal element 88. In other words, the proximal end of longitudinal element 88 may be coupled to front face 33 (e.g., to exit window 90), with the distal end of the longitudinal element coupled to the optical filter. (For embodiments in which eye-stabilizing structure 76 (FIG. 1) is used, longitudinal element 88 typically passes through the eye-stabilizing structure.) Typically, the longitudinal element is parallel to optical path 92.

Typically, the distance between the front face of the optical unit and the optical filter, which is generally equal to the length of longitudinal element 88, is between 10 and 50 mm, and/or the distance between the optical filter and the eye is between 0.1 and 20 mm.

As yet another alternative, the optical filter may be coupled to the optical bench belonging to the optical unit. For example, the optical filter may be coupled to the optical bench downstream from the most downstream of the beam-directing elements, such as between beam combiner 56 and opening 58 (FIG. 2), such that the optical filter interposes between the most downstream of the beam-directing elements and the pupil of the eye.

Alternative Embodiments

In alternative embodiments, optical filter 70 is opaque both to the treatment beams and to the fixation light, i.e., the visible light transmitted by light source 66 (FIG. 2). For example, the optical filter may comprise a metal or ceramic disk. Although, in such embodiments, the optical filter inhibits both the visible light and the treatment beams from reaching the pupil of eye 25, eye 25 may nonetheless be oriented for treatment, as described immediately below. Hence, the optical filter may be manufactured more cheaply and easily, without compromising the safety and efficacy of the procedure.

For example, to allow eye 25 to fixate on the light source, the light source may be coupled to the optical bench parallel to or downstream from the optical filter. For example, the optical filter and the light source may each be coupled to the optical bench between the most downstream of the beam-directing elements and opening 58, such that (i) the optical filter interposes between the most downstream of the beam-directing elements and the pupil of the eye, and (ii) light source 66 is disposed next to optical path 92, parallel to or downstream from the optical filter. Alternatively, the light source may be disposed behind the optical filter, as in FIG. 2; however, one or more reflectors coupled to the optical bench may reflect the fixation light through opening 58, such that the fixation light may reach eye 25 without needing to pass through the optical filter.

Alternatively, for embodiments in which eye 25 cannot see the fixation light through the optical filter, eye 25 may be oriented by causing the untreated eye of the patient to fixate on light source 66. In such embodiments, prior to the procedure, the patient is instructed to fixate the untreated eye on the light source. Subsequently, by virtue of the light source transmitting visible light, the untreated eye fixates on the light source, such that eye 25, by virtue of moving in tandem with the untreated eye, gazes approximately along optical path 92. Thus, while the untreated eye fixates on the fixation target, the treated eye may be irradiated with the treatment beams.

Figure 7:
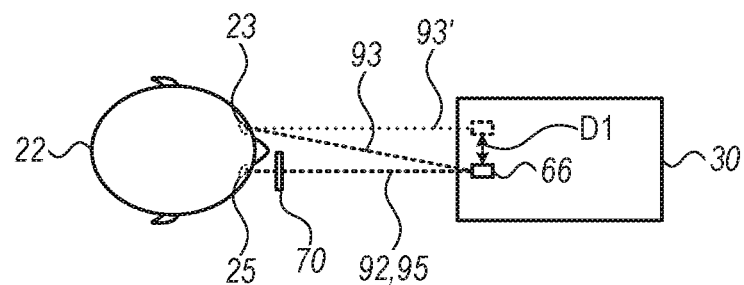
FIG. 7 is a schematic illustration of a technique for orienting an eye for treatment, in accordance with some embodiments of the present invention.

In this regard, reference is now made to FIG. 7, which is a schematic illustration of an alternative technique for orienting eye 25 for treatment, in accordance with some embodiments of the present invention. (FIG. 7 shows a schematic overhead view of optical unit 30 and patient 22.)

In some embodiments, the position of the light source is adjustable. For example, the light source may be mounted on a slider, such that the distance of the light source from optical path 92 is variable. In such embodiments, to facilitate orienting eye 25 via the fixation of the untreated eye 23 of the patient on the light source, the position of the light source is varied responsively to the degree to which the patient's eyes can converge onto the light source.

For example, for those patients, such as younger patients, whose eyes can converge onto light source, the light source may be aligned, at least approximately, with optical path 92, as described above with reference to FIG. 2. As untreated eye 23 fixates on the light source along a first line-of-sight 93, eye 25 gazes toward the light source along a second line-of-sight 95, which is approximately coincident with optical path 92.

For other patients, particularly older patients, whose eyes cannot converge onto the light source due to the relatively small distance between the patient and the light source, the light source may be displaced from the optical path towards the untreated eye, typically along an axis parallel to the interpupillary axis of the patient. For example, the light source may be placed at a distance D1 from the optical path that is approximately equal to the interpupillary distance of the patient; thus, for example, D1 may be between 45 and 80 mm. During the procedure, the untreated eye fixates on the light source along an alternate first line-of-sight 93', such that second line-of-sight 95 is approximately coincident with optical path 92.

In other embodiments, a single position of the light source is used for all patients. For example, the light source may be displaced from the optical path towards the untreated eye, typically along an axis parallel to the interpupillary axis of the patient, by a distance that is less than, such as 30%-70% of, an average or median interpupillary distance for a suitable population of patients. For example, assuming an average interpupillary distance of 62 mm, the light source may be displaced from the optical path by between 18 and 44 mm. Advantageously, this position may help second line-of-sight 95 to be sufficiently coincident with optical path 92, regardless of the degree to which the patient's eyes converge onto the light source.

Protecting the Eye During Treatment

Figure 8:
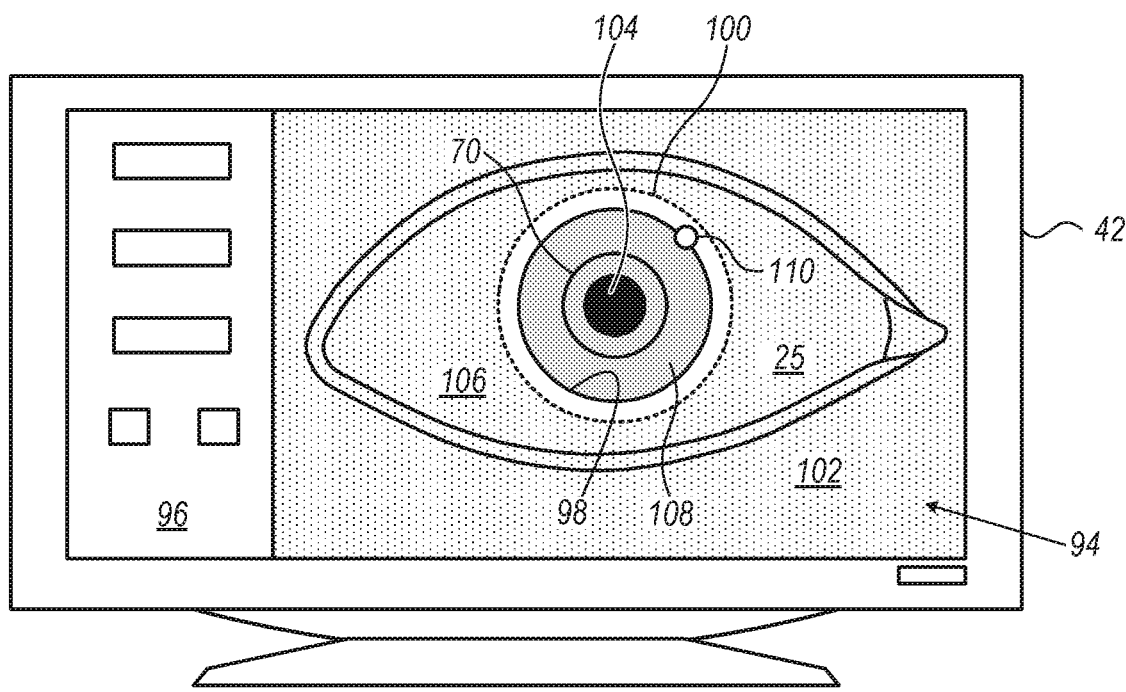
FIG. 8 is a schematic illustration of an image of an eye treated in accordance with some embodiments of the present invention.

Reference is now made to FIG. 8, which is a schematic illustration of an image 94 of eye 25 treated in accordance with some embodiments of the present invention.

Prior to the procedure, the camera acquires image 94. Based on the image, the user defines one or more target regions 110 of the eye that are to be irradiated. Typically, as described in International Patent Application PCT/IB2019/055564, target regions 110 are defined semi-automatically, based on input from the user via a graphical user interface (GUI) 96 displayed on monitor 42. Typically, at least part of each target region is located near (e.g., within 2 mm of) the limbus 98 of the eye; for example, each target region may overlap limbus 98.

Typically, following the definition of the target regions, the controller executes a mock trabeculoplasty by causing radiation source 48 (FIG. 2) to sweep an aiming beam across the target regions. Alternatively, the aiming beam may be emitted by an additional radiation source, such as a lower-power laser, that is collinear with radiation source 48. (Typically, the aiming beam differs from the treatment beams at least in that the energy of the aiming beam is subtherapeutic.) While this sweep is performed, camera 54 (FIG. 2) acquires images of the eye at a relatively high frequency and the images are displayed on monitor 42, such that the user may validate the target regions. Alternatively or additionally, for embodiments in which structure 76 (FIG. 1) does not have a continuous wall, the user may view the aiming beam, as it impinges on the eye, through an opening in the structure.

Following the validation of the target regions, the user starts the procedure, typically by entering an appropriate input via GUI 96. Subsequently, as described above with reference to FIG. 1, the target regions of the eye are irradiated by radiation source 48, i.e., the radiation source fires respective treatment beams at the target regions.

In some embodiments, during the procedure, the camera acquires images of the eye at a relatively high frequency (e.g., at a frequency greater than 40 Hz or 50 Hz). Based on the images, controller 44, by executing image-processing software, tracks motion of the eye, e.g., by identifying the center of the limbus in each image. Based on the motion tracking, the controller, prior to the irradiation of each target region, locates the target region in the FOV of the camera, and then controls the beam-directing elements such that a treatment beam impinges on the target region. In other embodiments, the eye-stabilizing structure may sufficiently stabilize the eye such as to obviate the need for high-frequency motion tracking. In such embodiments, during the procedure, the camera may acquire images of the eye, and the controller may check for movement of the eye, at a lower frequency; alternatively, the image acquisition and motion tracking may be omitted entirely. Similarly, high-frequency motion tracking may be omitted if only a small number of treatment beams are fired. For example, the radiation source may emit a single treatment beam—shaped, for example, as an ellipse or an arc—that simultaneously irradiates all the target regions.

In any case, regardless of whether high-frequency motion tracking is performed, embodiments of the present invention, as an extra precaution, protect the eye from any (unlikely) misaimed treatment beams that deviate too far from the limbus. Such protection may be effected using optical filter 70, which was described at length above. In particular, optical filter 70 may protect the retina of the eye by covering the pupil 104 of the eye. As described above with reference to FIG. 2, optical filter 70 may also cover at least part of the cornea 108 surrounding the pupil, thus protecting cornea 108. Alternatively or additionally, a peripheral optical filter, such as optical filter 86 belonging to optic 84 (described above with reference to FIGS. 4A-B), may protect the sclera 106 of the eye by covering sclera 106.

In some embodiments, the optical filter is opaque to the camera (i.e., to the frequencies to which the camera is sensitive). In such embodiments, the controller may identify the optical filter in the images acquired by the camera, and may further verify that the optical filter is covering the pupil, e.g., as described above with reference to FIG. 2. In other embodiments, the optical filter is transparent to the camera. (FIG. 8 assumes that the optical filter is transparent to the camera; nevertheless, for clarity, the edge of the optical filter is shown in FIG. 8.)

In some embodiments, alternatively or additionally to using an optical filter, the eye is protected using a virtual filter, implemented in the software and/or firmware run by the controller. In particular, prior to the firing of any treatment beams, controller 44 (FIG. 1) causes camera 54 to acquire image 94. Subsequently to the acquisition of image 94, the controller, based on the image, identifies one or more static regions in the FOV of the camera that include non-targeted portions of the eye. Subsequently, prior to the irradiation of each target region of the eye (i.e., prior to the firing of a treatment beam at the target region), the controller ascertains that the target region is not within any of the static regions. In response to ascertaining that the target region is not within any of the static regions, the controller causes the radiation source to irradiate the target region; otherwise, the treatment beam is not fired. Furthermore, in some embodiments, the controller inhibits the beam-directing elements from being aimed at any of the static regions even while the radiation source is inactive.

For example, as described in International Patent Application PCT/IB2019/055564, based on image 94, the controller may identify a central static region encompassing pupil 104 in the image. Subsequently, the controller may inhibit the radiation source from firing any treatment beams at the central static region. The central static region may thus protect the retina of the eye in the event that optical filter 70 is not used, or provide extra protection to that provided by the optical filter.

Alternatively or additionally, controller may identify a peripheral static region 102 that, in the image, is outside limbus 98 of the eye. Static region 102 may protect sclera 106 in the event that a peripheral optical filter is not used, or provide extra protection to that provided by a peripheral optical filter. As shown in FIG. 8, the peripheral static region may further protect the eyelids of the eye, along with other nearby tissue.

Typically, the peripheral static region includes the portion of the camera's FOV lying outside an elliptical (e.g., circular) boundary 100, which, in image 94, may be located outside limbus 98 at a distance of between 1 and 5 mm from the limbus.

It is emphasized that each of the static regions is "static" by virtue of being defined in terms of the FOV of the camera, such that the position of the region is not adjusted by the controller even in response to detected motion of the eye. Thus, the eye is protected even in the event of an (unlikely) error in the motion tracking performed by the controller.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
an optical unit, comprising:
a light source configured to transmit visible fixation light;
one or more beam-directing elements; and
a radiation source, configured to irradiate an eye of a patient with one or more treatment beams having a wavelength between 500 and 850 nm by emitting the treatment beams toward the beam-directing elements, which direct the one or more treatment beams toward the eye, while the eye fixates on the light source by virtue of the light source transmitting the visible fixation light, which has another wavelength different from the wavelength of the treatment beams; and
an optic, comprising:
an optical filter configured to inhibit passage of the treatment beams, but not the visible fixation light, therethrough, while interposing between the beam-directing elements and a pupil of the eye; and
a transparent portion that surrounds the optical filter and is transparent to the treatment beams.

2. The apparatus according to claim 1, further comprising an eye-stabilizing structure, wherein the radiation source is configured to irradiate the eye by emitting the treatment beams through the structure, and wherein the optic is coupled to the structure.

3. The apparatus according to claim 2, wherein a proximal end of the structure is configured to couple to the optical unit.

4. The apparatus according to claim 2, wherein the optic is coupled to a distal end of the structure.

5. The apparatus according to claim 4, wherein the optic is configured to contact the eye.

6. The apparatus according to claim 2, wherein a distal end of the structure is configured to contact the eye, and wherein the optic is mounted to an inner wall of the structure.

7. The apparatus according to claim 6, wherein the optic is mounted between 0.5 and 20 mm from the distal end of the structure.

8. The apparatus according to claim 6, wherein the distal end of the structure comprises a contact optic configured to contact the eye.

9. The apparatus according to claim 6, wherein the distal end of the structure comprises a contact ring configured to contact the eye.

10. The apparatus according to claim 6, further comprising one or more longitudinal elements extending between the inner wall of the structure and the optic, the optic being mounted to the inner wall via the longitudinal elements.

11. The apparatus according to claim 2, wherein an inner wall of the structure is configured to absorb the treatment beams.

12. The apparatus according to claim 1, wherein the optical filter is configured to inhibit the passage of the treatment beams by absorbing the treatment beams.

13. The apparatus according to claim 1, wherein the optical filter is configured to inhibit the passage of the treatment beams by reflecting the treatment beams.

14. The apparatus according to claim 1, wherein the optical filter comprises an anti-reflective surface configured to reduce reflection of the treatment beams.

15. The apparatus according to claim 1,
wherein the optical filter is a first optical filter, and
wherein the optic further comprises a second optical filter that surrounds the transparent portion and is configured to inhibit the passage of the treatment beams.

16. The apparatus according to claim 1, wherein the optic is configured to contact the eye.

17. The apparatus according to claim 16, wherein a thickness of the optic is less than 2 mm.

18. The apparatus according to claim 16, wherein a diameter of the optic is less than 10 mm.

19. The apparatus according to claim 1,
wherein the optical unit comprises a front face, which faces toward the eye of the patient, and
wherein the optic is coupled to the front face.

20. The apparatus according to claim 19,
wherein the front face comprises an exit window,
wherein the light source is configured to transmit the visible fixation light, and the radiation source is configured to emit the treatment beams, through the exit window, and
wherein the optic overlays the exit window.

21. The apparatus according to claim 19,
wherein the front face comprises an exit window,
wherein the light source is configured to transmit the visible fixation light, and the radiation source is configured to emit the treatment beams, through the exit window, and
wherein the optic is embedded within the exit window.

22. The apparatus according to claim 19, further comprising a longitudinal element extending between the front face and the optic, the optic being coupled to the front face via the longitudinal element.

23. The apparatus according to claim 22,
wherein the front face comprises an exit window,
wherein the light source is configured to transmit the visible fixation light, and the radiation source is configured to emit the treatment beams, through the exit window, and
wherein the longitudinal element extends between the exit window and the optic.

24. A method, comprising:
interposing an optic, which includes an optical filter and a transparent portion that surrounds the optical filter, between one or more beam-directing elements and a pupil of an eye of a patient; and
while the optic interposes between the beam-directing elements and the pupil:
using a light source, transmitting visible fixation light through the optical filter; and
while the eye fixates on the light source by virtue of the light source transmitting the visible fixation light, irradiating the eye with one or more treatment beams having a wavelength between 500 and 850 nm by emitting the treatment beams toward the beam-directing elements, which direct the one or more treatment beams toward the eye and through the transparent portion of the optic, which is transparent to the treatment beams,
the optical filter being configured to inhibit passage of the treatment beams but not the visible fixation light, which has another wavelength different from the wavelength of the treatment beams, therethrough.

25. The method according to claim 24, wherein the optic is coupled to an eye-stabilizing structure, and wherein irradiating the eye comprises irradiating the eye by emitting the treatment beams through the structure.

26. The method according to claim 25, wherein the light source and the beam-directing elements belong to an optical unit, and wherein emitting the treatment beams through the structure comprises emitting the treatment beams through the structure while a proximal end of the structure is coupled to the optical unit.

27. The method according to claim 25, wherein the optic is coupled to a distal end of the structure.

28. The method according to claim 27, wherein interposing the optic comprises interposing the optic by contacting the eye with the optic.

29. The method according to claim 25, wherein the optic is mounted to an inner wall of the structure, and wherein emitting the treatment beams through the structure comprises emitting the treatment beams through the structure while a distal end of the structure contacts the eye.

30. The method according to claim 29, wherein the optic is mounted between 0.5 and 20 mm from the distal end of the structure.

31. The method according to claim 29, wherein the optic is mounted to the inner wall via one or more longitudinal elements extending between the inner wall and the optic.

32. The method according to claim 24,
wherein the optical filter is a first optical filter, and
wherein the optic further includes a second optical filter that surrounds the transparent portion and is configured to inhibit the passage of the treatment beams.

33. The method according to claim 24, wherein interposing the optic comprises interposing the optic by contacting the eye with the optic.

34. The method according to claim 33, wherein a thickness of the optic is less than 2 mm.

35. The method according to claim 33, wherein a diameter of the optic is less than 10 mm.

36. The method according to claim 24,
wherein the light source and the beam-directing elements belong to an optical unit that includes a front face, which faces toward the eye of the patient, and
wherein the optic is coupled to the front face.

37. The method according to claim 36,
wherein the front face includes an exit window,
wherein transmitting the visible fixation light comprises transmitting the visible fixation light through the exit window,
wherein emitting the treatment beams comprises emitting the treatment beams through the exit window, and
wherein the optic overlays the exit window.

38. The method according to claim 36,
wherein the front face includes an exit window,
wherein transmitting the visible fixation light comprises transmitting the visible fixation light through the exit window,
wherein emitting the treatment beams comprises emitting the treatment beams through the exit window, and
wherein the optic is embedded within the exit window.

39. The method according to claim 36, wherein the optic is coupled to the front face via a longitudinal element extending between the front face and the optic.

40. The method according to claim 39,
wherein the front face includes an exit window,
wherein transmitting the visible fixation light comprises transmitting the visible fixation light through the exit window, wherein emitting the treatment beams comprises emitting the treatment beams through the exit window, and
wherein the longitudinal element extends between the exit window and the optic.

\* \* \* \* \*